United States Patent [19]
Kalyan et al.

[11] Patent Number: 5,376,547
[45] Date of Patent: Dec. 27, 1994

[54] DES-EPIDERMAL GROWTH FACTOR PLASMINOGEN ACTIVATORS

[75] Inventors: Narender K. Kalyan, King of Prussia; Shawguang L. Lee, Villanova; Paul P. Hung, Bryn Mawr, all of Pa.

[73] Assignee: American Home Products Corporation, Madison, N.J.

[21] Appl. No.: 150,267

[22] Filed: Jan. 29, 1988

Related U.S. Application Data

[63] Continuation-in-part of Ser. No. 8,795, Jan. 30, 1987, abandoned.

[51] Int. Cl.$^5$ .................... C12N 9/48; C12N 9/64; A61K 37/547
[52] U.S. Cl. .................... 435/226; 435/215; 435/212
[58] Field of Search .................... 435/212, 226, 215

[56] References Cited

U.S. PATENT DOCUMENTS

| | | | |
|---|---|---|---|
| 4,916,071 | 10/1990 | Hung | 435/212 |
| 5,002,887 | 3/1991 | Larsen | 435/212 |
| 5,071,972 | 12/1991 | Larsen | 536/23.5 |
| 5,106,741 | 4/1992 | Marotti | 435/226 |

FOREIGN PATENT DOCUMENTS

| | | | |
|---|---|---|---|
| 8655514 | 10/1986 | Australia. | |
| 0092182 | 10/1983 | European Pat. Off. | C12N 15/00 |
| 178105 | 4/1986 | European Pat. Off. | |
| 0196920 | 10/1986 | European Pat. Off. | |
| 207589 | 1/1987 | European Pat. Off. | |
| 242836 | 4/1987 | European Pat. Off. | C12N 15/00 |
| 240334 | 10/1987 | European Pat. Off. | |
| 241209 | 10/1987 | European Pat. Off. | |
| 241210 | 10/1987 | European Pat. Off. | C12N 15/00 |
| 872694 | 12/1987 | South Africa | C12N 15/00 |
| 8703906 | 7/1987 | WIPO. | |

OTHER PUBLICATIONS

Ny, T. et al., *PNAS*, 81, 5355 (1984).
Lee, S. et al., *J. Biol. Chem.*, 263 (6), 2917 (1988).
Pennica, D. et al., *Nature*, 310, 214 (1983).
Belin, D. et al., *Eur. J. Biochem*, 148, 225 (1985).
Lee, S. et al., *Thromb. Haemostasis*, 58, 313 (1987).
van Zonneveld, et al., –Autonomous functions of structural domains on human tissue–type plasminogen activator. Mar. 10, 1986.
Vehar, et al.–Characterization studies on human melanoma cell tissue plasminogen activator–Dec., 1984.

*Primary Examiner*—Garnette D. Draper
*Assistant Examiner*—Marianne Porta Allen
*Attorney, Agent, or Firm*—Richard K. Jackson

[57] ABSTRACT

Des-epidermal growth factor homologous—plasminogen activators with greatly diminished affinity for liver membranes.

11 Claims, 15 Drawing Sheets

Synthetic Finger Domain:

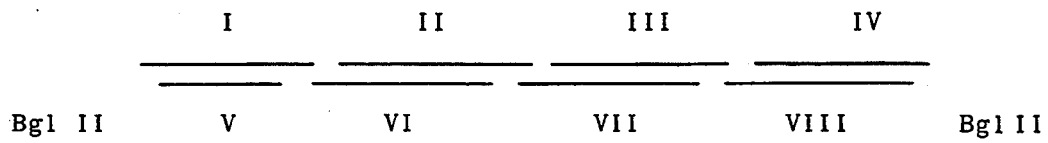

```
         I           II          III          IV
       _____     _____     _____     _____
       _____     _____     _____     _____
Bgl II   V          VI          VII         VIII       Bgl II
```

1. Kinase all 8 oligomers
2. Ligase
3. Cut with Bgl II
4. Isolate 132 bp DNA fragment

FIGURE 4A

|                | -1  | +1  | 2   | 3   | 4   | 5   | 6    | 7   | 8   |
|----------------|-----|-----|-----|-----|-----|-----|------|-----|-----|
| Aminoacids:    | Arg | Ser | Tyr | Gln | Val | Ile | Cys⁻ | Arg | Asp |
| Original Seq.: | GA  | TCT | TAC | CAA | GTG | ATC | TGC  | AGA | GAT |
| Modified Seq.: | GA  | TCC | TAT | CAG | GTC | ATT | TGT  | CGC | GAC |
|                |     | 3'-G| ATA | GTC | CAG | TAA | ACA  | GCG | CTG |

↑ Bgl II

| 9   | 10  | 11  | 12  | 13  | 14  | 15  | 16  | 17  | 18  | 19  |
|-----|-----|-----|-----|-----|-----|-----|-----|-----|-----|-----|
| Glu | Lys | Thr | Gln | Met | Ile | Tyr | Gln | Gln | His | Gln |
| GAA | AAA | ACG | CAG | ATG | ATA | TAC | CAG | CAA | CAT | CAG |
| GAG | AAG | ACC | CAA | ATG | ATC | TAT | CAA | CAG | CAC | CAA |
| CTC | TTC | TGG | GTT | TAC | TAG | ATA | GTT | GTC | GTG | GTT |

| 20  | 21  | 22  | 23  | 24  | 25  | 26  | 27  | 28  | 29  | 30  |
|-----|-----|-----|-----|-----|-----|-----|-----|-----|-----|-----|
| Ser | Trp | Leu | Arg | Pro | Val | Leu | Arg | Ser | Asn | Arg |
| TCA | TGG | CTG | CGC | CCT | GTG | CTC | AGA | AGC | AAC | CGG |
| TCT | TGG | CTC | AGG | CCC | GTC | CTG | CGC | TCA | AAT | AGA |
| AGA | ACC | GAG | TCC | GGG | CAG | GAC | GCG | AGT | TTA | TCT |

| 31  | 32  | 33  | 34  | 35  | 36  | 37  | 38  | 39  | 40  | 41  |
|-----|-----|-----|-----|-----|-----|-----|-----|-----|-----|-----|
| Val | Glu | Tyr | Cys | Trp | Cys | Asn | Ser | Gly | Arg | Ala |
| GTG | GAA | TAT | TGC | TGG | TGC | AAC | AGT | GGC | AGG | GCA |
| GTC | GAG | TAC | TGT | TGG | TGT | AAT | TCT | GGG | CGC | GCC |
| CAG | CTC | ATG | ACA | ACC | ACA | TTA | AGA | CCC | GCG | CGG |

| 42  | 43  | 44  | 45  |
|-----|-----|-----|-----|
| Gln | Cys | His | Ser |
| CAG | TGC | C   |     |
|     |     |     | Bgl II |
| CAA | TGT | A   |   ↓    |
| GTT | ACA | TCT | AG-5'  |

FIGURE 4B

```
          10         20         30
GGGAATTCCG GTACCCATTC CCTGACTGAA
  EcoRl   Kpnl 40         50         60
AGCGGCGCTA GCTGTCTGCC CTGGAACAGC 70         80         90
ATGATTCTCA TCGGTAAAGT CTATACCGCT 100        110        120
CAAAACCCAT CCGCTCAAGC TCTCGGTCTC 130        140        150
GGTAAGCACA ACTATTGAAG AAACCCCGAC 160        170        180
GGCGACGCTA AACCATGGTG TCATGTCCTC 190        200        210
AAAAACAGAC GCCTCACCTG GGAATATTGC 220        228
GACGTCCCAG AATTCCCG
Aatll       EcoRl
```

FIGURE 8

DES-EPIDERMAL GROWTH FACTOR PLASMINOGEN ACTIVATORS

This application is a continuation-in-part of copending U.S. patent application Ser. No. 8,795 filed Jan. 30, 1987, now abandoned.

BACKGROUND OF THE INVENTION

The plasminogen activators, tissue plasminogen activator (t-PA) and urokinase (u-PA), consist mainly of two parts, a catalytic part which is involved in the conversion of plasminogen to plasmin (a serine protease which degrades the fibrin network of a blood clot) and a non-catalytic part which contains the regulatory regions responsible for physiological specificity such as fibrin binding. Van Zonneveld et al., Proc. Nat'l. Acad. Sci. U.S.A., 83 4670-4674 (1986) has elucidated the functions of several structural domains of t-PA.

The non-catalytic part of t-PA contains at least three domain structures: two kringles of 82 amino acids each; an epidermal growth factor (EGF) region of 45 amino acids and a fibronection (finger) domain of 45 amino acids. Urokinase has a similar non-catalytic domain structure with a single kringle of 82 amino acids and no fibronection region.

The EGF domains of t-PA and u-PA share considerable regions of homology with the human epidermal growth factor sequence. Vehar et al., Bio/Technology, 1051-1057, December 1984 depicts these homologous regions in FIG. 7, page 1055. For example, the relative positions of five of the six cysteine residues, involved in disulfide bonding, are conserved. Similarly, several amino acids and amino acid sequences within the EGF domain of t-PA and u-PA correspond to the same positions in EGF; e.g. amino acids 52, 56–62, 67–69, 73–76, 79, 81 and 84–87.

Because of its high binding specificity for blood clot fibrin, t-PA is regarded as an ideal thrombolytic agent [Collen, Circulation, 72 1820 (1985)]. However, t-PA is very rapidly removed from the circulation by the liver ($t_{\frac{1}{2}}$=about 1 to 3 minutes), thereby reducing its effectiveness in the treatment of thrombotic vascular accidents [Emeis et al., Thrombosis and Haemostasis, 54 (3), 661–664 (1985)]. Fuchs et al., Blood, 65 (3) 539–544 (1985) demonstrated that urokinase (u-PA) is similarly removed from the circulation by the liver and that these plasminogen activators are cleared by a process not dependent upon the proteinase active site. The hepatocyte was shown to be the cell-type responsible for rapid t-PA clearance. Rijken et al., Biochem. J. 238 643–644 (1986) found that the light chain of t-PA (C-terminal portion) was much less rapidly cleared from the circulation than the heavy chain, establishing the heavy chain as containing the polypeptide sequence recognized by the liver. The binding of t-PA and urokinase to liver membranes is fast and is not inhibited by asialo-fetuin (terminal galactose), mannan or fibrinogen, suggesting that carbohydrates do not mediate its clearance from the blood.

DESCRIPTION OF THE INVENTION

It has now been discovered that it is the EGF domain of t-PA and urokinase which is responsible, solely or in combination with some non-elucidated region of these polypeptides, for binding to liver membranes, which explains their rapid clearance from circulation. As a result of this discovery, plasminogen activators with markedly reduced affinity for liver membranes have been developed by modification of the N-terminal portion; i.e., EGF and fibronectin domain, of t-PA, u-PA and hybrid plasminogen activators (h-PA) such as are disclosed in U.S. Pat. No. 4,916,074. Thus, this invention provides novel plasminogen activators in which the EGF region has been removed, the fibronectin and EGF regions have been removed, and in which one or more fibronectin regions have been added to des-EGF u-PA, to des-EGF t-PA, or des-EGF h-PA. These polypeptides are prepared by genetic engineering techniques using cDNA clones of t-PA and u-PA genes.

Furthermore, it has been discovered that the entire EGF domain need not be removed from the DNA encoding for a desired plasminogen activator. Deletion of polynucleotides corresponding to amino acids 55–62 effectively alters the resulting polypeptide and avoids recognition (binding, metabolism) by liver membranes. Other modifications of the EGF domain of DNA encoding for plasminogen activators include deletion of the nucleotides which produce EGF homologous amino acids 55–62; modification of one or more cysteine sites as by replacement with codons generating methionine, serine, alanine, etc. to disrupt the tertiary structure of the EGF domain; or replacement of nucleotides for neutral amino acids such as a.a. 60 (glycine), with codons generating charged amino acids such as aspartic acid, lysine, arginine, and the like. Plasminogen activators produced from DNA modified in this manner pass through the liver and are returned to the bloodstream in functionally active form. All of these modifications are readily performed by oligonucleotide directed (or site specific) mutagenesis after cloning of the plasminogen activator gene into a single stranded DNA vector such as bacteriophage M13. (Zoller et al., Methods in Enzymology, 100, 468-500, 1983).

The modified plasminogen activators resulting from this invention are best described as des-EGF homologous plasminogen activators. By the expression "EGF-homologous" applicants mean that the EGF region of the product has been so modified by deletion, addition, or substitution of one or more amino acids that the relevant functional properties of that region cease to exist as they relate to binding by liver membranes and removal from blood circulation.

DESCRIPTION OF THE DRAWINGS

FIGS. 4(a) and 4(b) presents (a) a map and (b) 132 base pair DNA sequence of the finger domain insert coding for amino acids 1–44 of t-PA employed in FIG. 5.

FIG. 8–10a presents a flow diagram of the method of preparing p5'HybF-5 and the oligonucleotide synthetically prepared to encode amino acids 191–258 found in K2 of t-PA used in production of that plasmid.

In FIG. 11, E represents EcoO 109.

Figure 1:
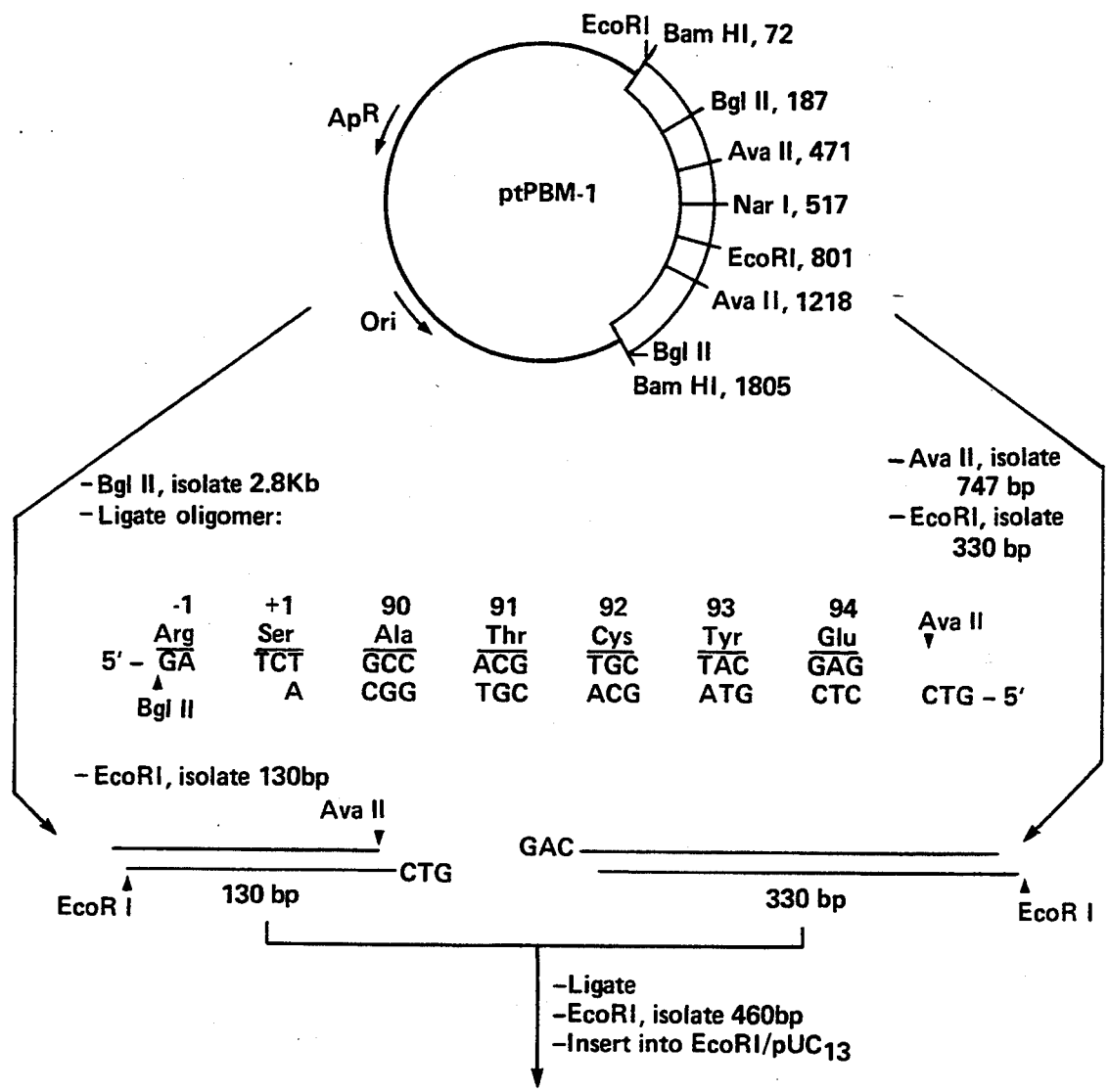
FIGS. 1 and 1a presents a flow diagram of the method employed in the production of the gene coding for $\Delta_{2-89}$ t-PA.
Figure 1A:
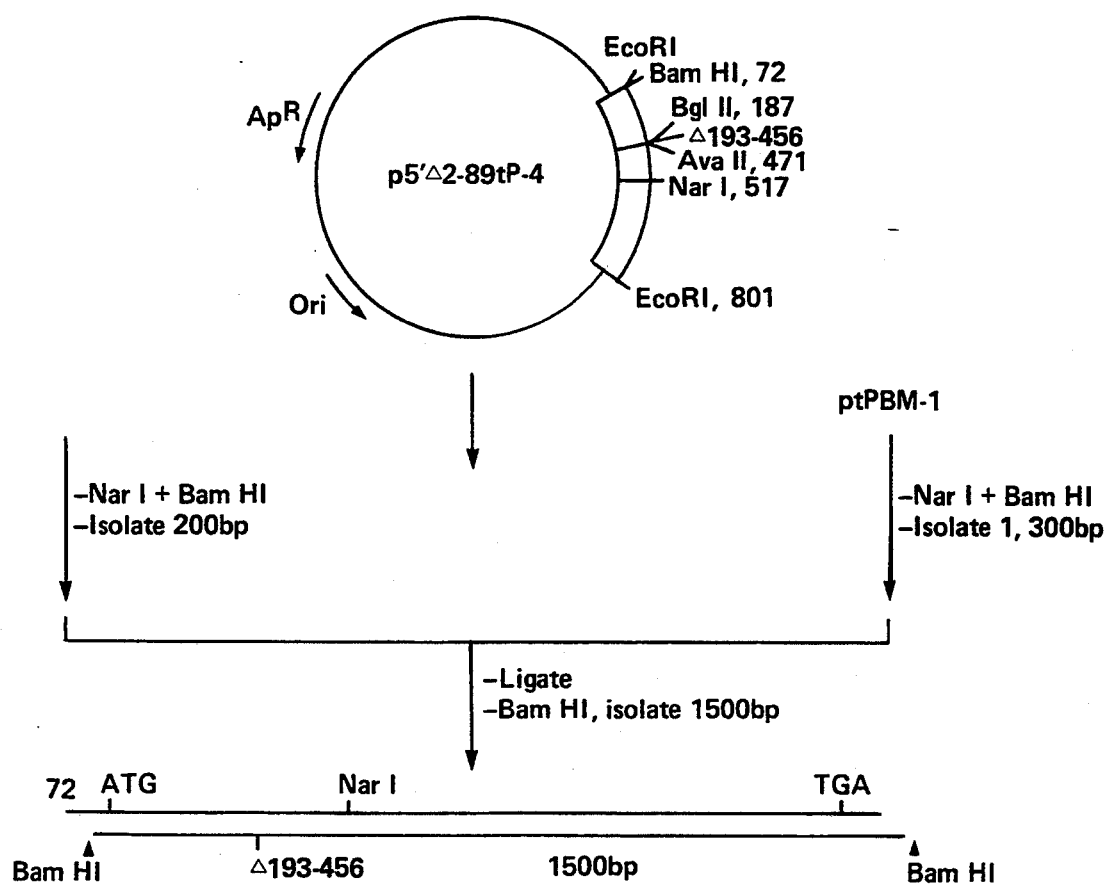
Figure 2:
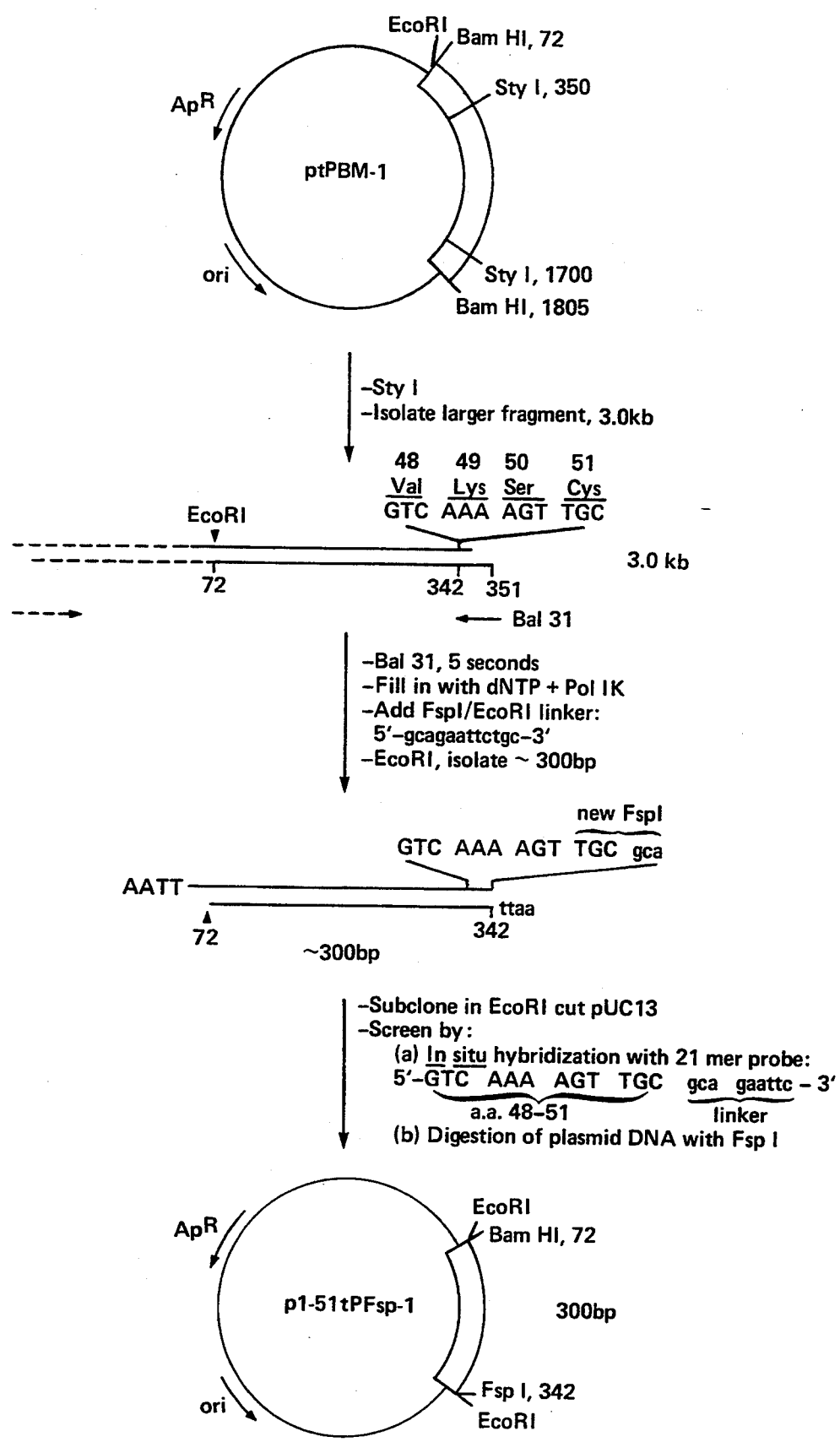
FIGS. 2 and 2a presents a flow diagram of the method employed in the production of the gene coding for $\Delta_{EGF}$ t-PA.
Figure 2A:
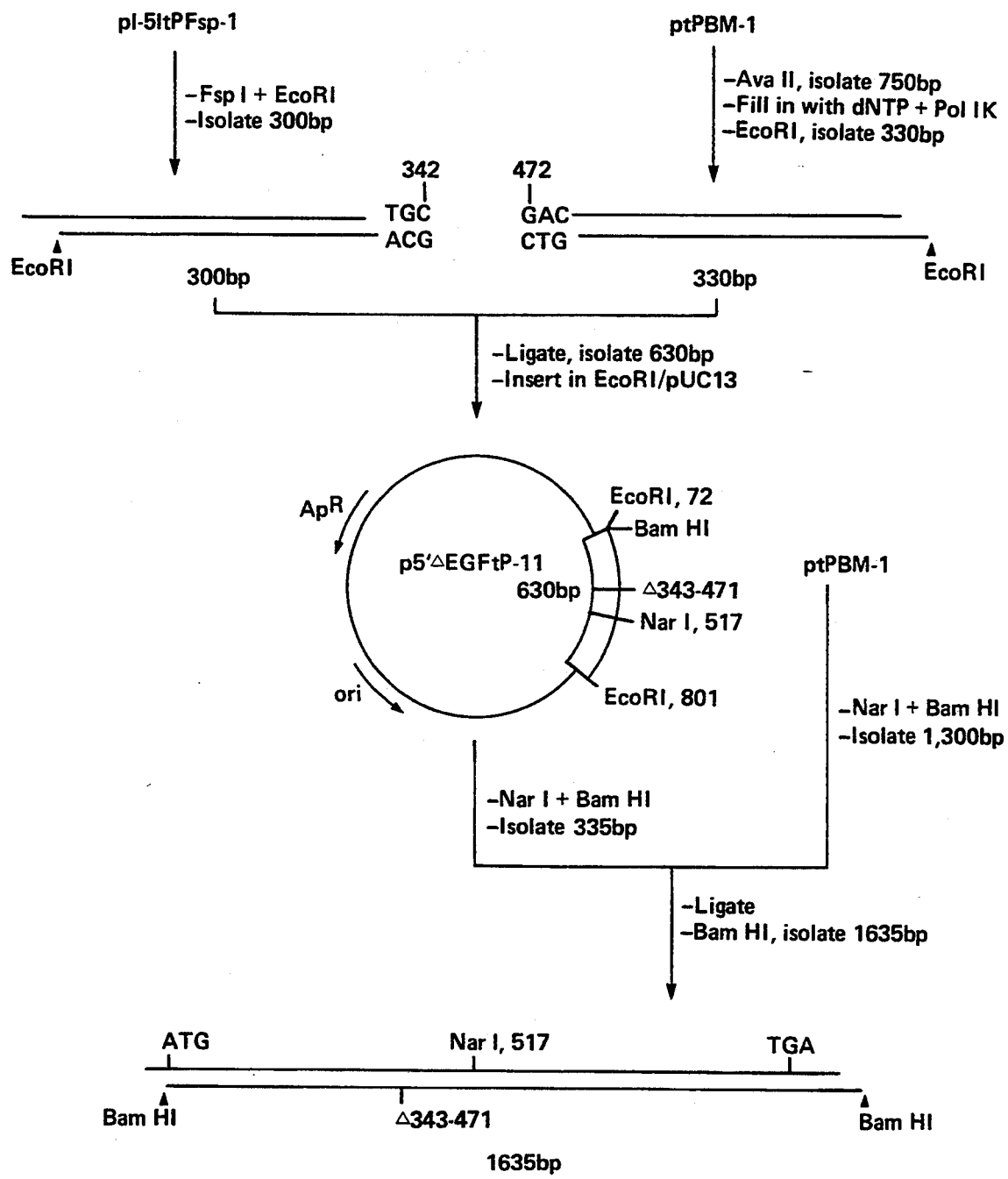
Figure 3:
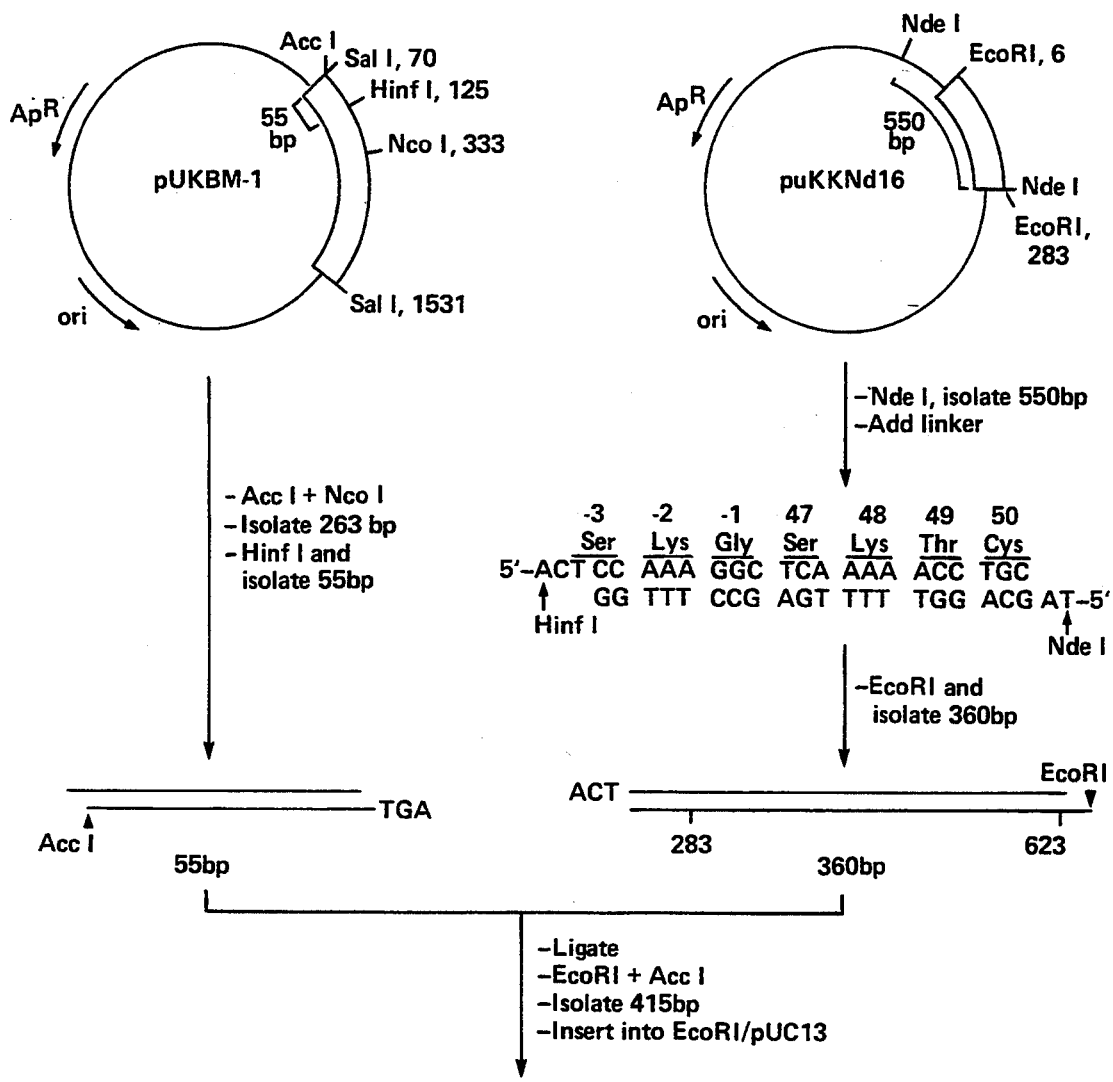
FIGS. 3 and 3a presents a flow diagram of the method employed in the production of the gene coding for $\Delta_{EGF}$ u-PA.
Figure 3A:
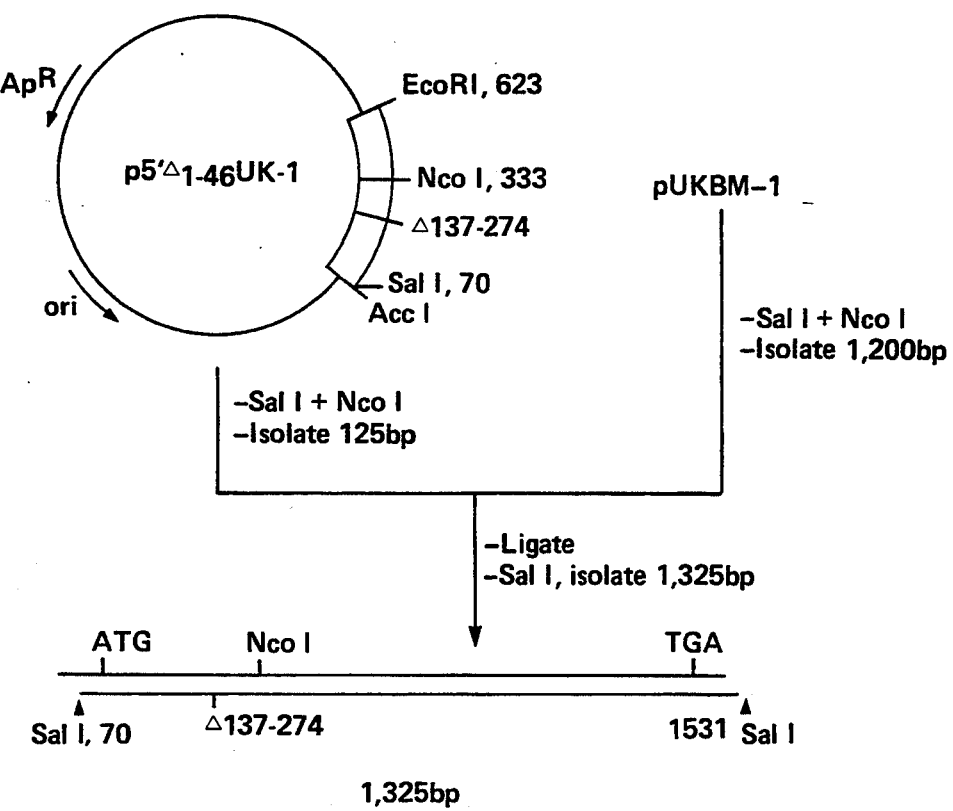
Figure 5:
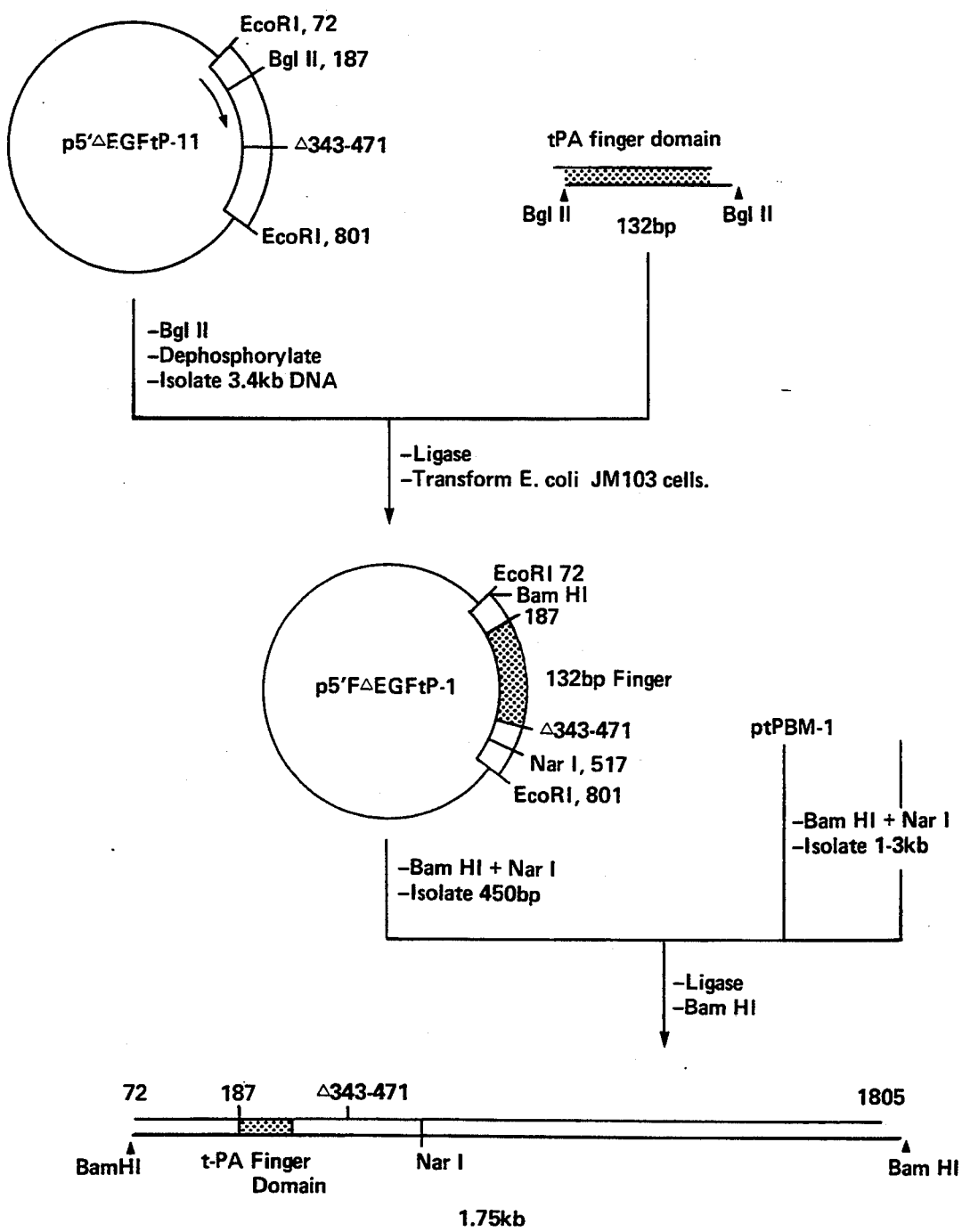
FIG. 5 presents a flow diagram of the method employed in production of the gene coding for $\Delta_{EGF}$-bi-(a.a$^{1-44}$) t-PA.

METHODS AND MATERIALS a) Enzymie Reactions: The restriction and DNA modifying enzymes were obtained from New England Biolabs Inc., Beverly, Mass. or International Biotechnologies Inc., New Haven, Conn. A typical restriction enzyme reaction was performed in a total volume of 50 μl containing 100–200 ng DNA and 400 units of T4 DNA ligase (N.E. Biolabs.). For blunt end ligation, 4 units of T4 RNA ligase (N.E. Biolabs.) are included in the above reaction mixture. (Goodman, H. M., and MacDonald, R. J., Method. Enzymol. 68, 75, 1979). The buffer solution used is prepared as a stock 10X solution; 0.5 M Tris®.HCl (pH 7.6), 0.1 M MgCl$_2$ and 0.1 M DTT (dithiothreitol).

b) Synthesis of Oligonucleotides: All the oligonueleotides mentioned in this application were synthesized by the phosphotriester method (Crea et al., Proc. Nat'l. Acad. Sci. (USA) 75, 5765, 1978)using the Gene Machine model 380A (Applied Biosystems Inc., Foster City, Calif.). Before their use in ligation reactions, the oligomers were phosphorylated at the 5' end in a volume of 50 μl containing 200–500 ng DNA, 10 units of T4 DNA kinase, 0.5 mM ATP and kinase buffer (0.05 M Tris.HCl, pH 7.6, 10 mM MgCl$_2$, 5 mM DTT) and incubated at 37° C. for ½ hour. For use as hybridization probes, oligomers were radiolabeled with 100 μCi gamma $^{32}$P-ATP (5,000 Ci/mmol, Amersham, Arlington Heights, Ill.) following the procedure of Maxam, A. M. and Gilbert, W. Method Enzymol. 65, 499 (1980).

c) Isolation of DNA Fragments: DNA fragments were first separated by electrophoresis through 0.5–1.5% agarose gel. Electrophoresis is carried out at about 100 volts for 2–4 hours in Tris-Borate-EDTA (TBE) buffer (0.089M Tris, 0.089M boric acid, 2 mM EDTA, pH 8.0). DNA bands are visualized under UV light by staining the gel with 0.5 μg/ml ethidium bromide solution (Sharp et al. Biochem. 12, 3055, 1973). The agarose containing the DNA band is cut out with a razor. The DNA is electroeluted from the gel. (Maniatis et al. Molecular Cloning, a Laboratory Manual, p. 164, 1982). The DNA is further purified by passing it through an Elutip-d ® column (Sehleieher and Sehuell, Keene, N.H.). The DNA is precipitated with ethanol. After centrifugation in an Eppendorf microfuge for 15 minutes, the pellet is washed once with 70% ethanol, dried under vacuum and dissolved in 50 μl deionized water.

d) Miniplasmid DNA Preparation: About 2 ml of LB (Luria Bertani) medium containing appropriate antibiotics is inoculated with a single bacterial colony and is incubated at 37° C. overnight with vigorous shaking. About 1.5 ml of the culture medium is used to isolate plasmid DNA by the boiling method described in Maniatis et al., loc. cit. p. 366. The rest of the culture is stored in 15% glycerol at −20° C. for later use. The DNA is dissolved in 40 μl H$_2$O containing 10 μg RNAse/ml. About 8 μl is sufficient for one restriction enzyme analysis.

e) Large Scale Preparation of Plasmid DNA: Typically, one liter of LB medium is inoculated with a single bacterial colony. After amplification of the plasmid DNA with chloramphenicol, the bacterial cells are harvested and lysed according to the boiling method (Holmes, D. S. and Quigley, M. Anal. Biochem. 114, 193, 1981). The plasmid DNA is further purified either by cesium chloride gradient centrifugation or by column chromatography on a Sepharose 4B column (Pharmacia, Uppsala, Sweden) as described in Maniatis et al., loc. cit. pp. 93–96. A recovery of about 400 μg DNA per liter culture is routinely obtained.

f) Vectors: Oligo-dG-tailed pBR322 plasmid DNA (Bethesda Research Laboratories, Inc., Gaithersburg, Md.) was used to clone the cDNA for t-PA and u-PA. The detailed molecular structure of pBR322 is described by Maniatis et al., loc. cit. pp. 5 and 488. The E. coli strains used for transformation with recombinant pBR322 were either HB101 or 294 (Maniatis et al., loc. cit. p. 504). The plasmid pBS M13$^-$used in production of some of the Δ$_{55-62}$ plasminogen activators was obtained from Stratagene, San Diego, Calif.

All subcloning of DNA fragments from t-PA and u-PA genes were performed in pUC plasmids—a series of pBR322 derived vectors containing lac Z and ampicillinase genes. These plasmids also contain multiple cloning sites in the lac Z region, which provides great flexibility in subcloning of DNA sequences (Vieria, J. and Messing, J., Gene 19, 259, 1982). Cloning in any of the available 11 sites can be monitored by the appearance of white recombinant colonies in the background of blue vector colonies on an indicator plate containing X-gal (5-bromo-4-chloro-3-indolyl β-D-galactoside) (Ruther, Mol. Gen. Genetics 178, 475, 1980). The E. coli strain used for transformation with the recombinant pUC plasmid was JM 103. The pUC plasmid and E. coli JM 103 were obtained from Pharmacia Inc., Piscataway, N.J.

g) Host/vector System

1. Microbial System

The work described here was performed using the microorganisms E. coli -12 strain JM 103 (Pharmacia) and E. coli K-12 strain 294 (ATCC No. 33625). Other microorganisms which may be used in this process include other useful E. coli strains and Bacilli, such as *Bacillus subtilis*. All these microorganisms utilize plasmids that can replicate and express heterologous gene sequences.

The expression system in yeast employs a plasmid which is capable of selection and replication in E. coli and/or yeast (Saccharomyces cerevisiae). For selection in yeast, the plasmid contains the TRP 1 gene which renders a transformed trp- yeast strain (RH218) prototrophic for tryptophan. The yeast expression vector can shuttle between yeast and E. coli. The plasmid has the following components: (1) a DNA segment derived from PBR 322 containing the origin of replication and the ampicillin resistance gene, (2) the yeast TRP 1 gene, (3) the yeast 2 μ DNA which enables the plasmid to replicate in yeast with high stability, (4) a promoter region from the yeast gene, such as alcohol dehydrogenase, α factor, glyceraldehyde-3-phosphatedehydrogenase, etc., (5) translational start and transcriptional stop sequences which can be used for proper termination and polyadenylation of mRNA in the expression system.

2. Mammalian Cell Culture System

Mammalian cell lines capable of the replication and expression of a compatible vector for the production of heterologous proteins can be used in the present invention. They are, for example: Cos-7, WI38, 3T3, CHO, Hela cells, and C127 cells. The vectors used contain (1) the origin of replication derived from a virus (SV40, adeno, polyoma, BPV) or cellular chromosomal DNA, (2) a promoter, (3) the translational initiation signals, such a ribosomal binding sites, and (4) RNA processing signals, (RNA splicing, polyadenylation and transcriptional terminator sequences). Specific examples of the expression vectors presented here use a BPV viral replication origin, a mouse metallothionein promoter and SV40 RNA processing signals. The vector can also be shuttled between a mammalian cell culture and E. coli. It contains derivatives of pBR322 sequences which provide selectable markers for E. coli ampicillin resistance as well as an E. coli origin of DNA replication. These sequences are derived from the plasmid pML-2d.

The edited hybrid plasminogen activator gene containing a Bam H1 sticky end is first inserted at the Bgl II site of plasmid 341-3 (Law MF et al., Md. Cell Biol. F 3, 2110, 1983) between the mouse metallothionein transcriptional promotor element and the SV40 early region transcriptional processing signals. The complete BPV genome, obtained after digestion of plasmid 142-6 (ATCC No. 37134) with Bam H1, is ligated to the unique Bam H1 site. Plasmid 341-3 also contains pML2, a pBR322 derivative which allows plasmid replication in bacterial cells. The expression plasmid constructed herein can replicate in mouse C127 cells exclusively as an extrachromosomal episome. Transfected cells can be selected for the transformed phenotype. Further modification of the expression vector, such as by adding specific enhancer elements for higher expression levels or inserting drug resistance (such as neomycin resistance) into the gene is also possible.

$\Delta_{EGF}$ Plasminogen Activators

The starting point for preparation of the plasminogen activators devoid of the epidermal growth factor domain which are specifically exemplified herein, is based upon the plasmids ptPBM1, pUKBM and pUKKNd16.

Messenger RNA for t-PA

Total RNA was isolated by the isothioeyanate method (Maniatis et al., Molecular Cloning, a Laboratory Manual, p. 196, 1982) from normal human fibroblast cells (WI-38 cells), which had been stimulated by endothelial cell growth factor (ECGF) and heparin to produce t-PA. The same stimulated cells produce urokinase. Messenger RNA (mRNA) was obtained from the total RNA by chromatography on an oligo-deoxy-thymidine (dT)-cellulose column (Aviv et al., Proc. Nat'l. Acad. Sci. USA, 69, 1408, 1972). Further fractionation of the mRNA was performed by centrifugation in a 15–30% sucrose density gradient and individual mRNA fractions were hybridized with $^{32}P$-probes as described below. Fractions containing the t-PA message (ca. 20–24S) were pooled for use in the preparation of complementary DNA (cDNA).

Complementary DNA for t-PA

The pooled mRNA (5 μg) described in the previous paragraph was used to produce double stranded cDNA and the cDNA was homopolymer tailed with polydeoxycytidylate (poly dC) using terminal nucleotide transferase. The product was annealed with Pst 1 digested, polydeoxyguanylate (poly dG) tailed pBR322. The annealed DNA was used to transform competent E. coli 294 cells which were cultured to produce about $10^5$ bacterial clones (Maniatis et al., loc cit., p. 229).

Screening and Identification of t-PA Clone

The following three oligonueleotides, after radiolabeling with $^{32}P$-ATP, were used to screen the library of recombinant clones. These oligomers correspond to amino acid sequences, 34–39 (17 mer), 253–258 (18 mer) and 523–527 (15 mer) of the t-PA molecule (Pennica, D. et al., Nature, 301 214, 1983) 17 mer: 5'-CCACTGTT-GCACCAGCA-3'; 18 mer: 5'-CACATCACAG-TACTCCA-3'; 15 mer: 5'CGGTCGCATGTTGTC-3'. About 20 colonies exhibited moderate to strong homology with the pooled probes. Replating and rehybridization of these colonies gave 16 clones with positive signals. Plasmid DNA prepared from these clones was blotted on nitrocellulose paper and hybridized with individual probes. Two clones (42 and 62a) hybridized to both the middle (18 mer) and 3' end (15 mer) probes. Enzymatic digestion of plasmid DNA with Pst 1 showed that clone No. 42 contained the biggest insert of greater than 2 kilobase (Kb) in the form of three fragments of 1.1, 0.6 and 0.4 Kb. This clone contains the full length sequence for the t-PA gene, containing 2600 bp, which includes the 5'- and 3'-untranslated regions.

ptPBM-1

Approximately 10 μg of pWP 42 plasmid DNA was digested with 9 units Xho II at 37° C. for 2 hours. The reaction mixture was run on preparative 1.2% agarose gel and a 1618 bp DNA fragment was isolated by electrophoresis in agarose gel. After filling in cohesive ends with E. coli Polymerase 1 (Klenow fragment) and dNTPs (four deoxy nucleotide triphosphates- dATP, dGTP, dCTP and dTTP) 1 μg of the so modified DNA was ligated overnight with 300 ng of phosphorylated Sal 1 linker. After phenol/chloroform extraction and ethanol precipitation, the DNA was digested with 50 U of Sal 1 for four hours and the reaction mixture applied to a preparative 1% agarose gel to isolate the desired DNA fragment.

The DNA with Sal 1 ends was ligated to Sal 1 cut pUC 13 and used to transform E. coli JM 103 cells and the cells were plated out on ampicillin and X-gal plates. Eight ampicillin resistant, white colonies were selected and grown to prepare a mini-plasmid preparation. Two clones (ptPS34B and ptPS39) were found to contain the required DNA fragment. Ten μg of ptPS39 plasmid DNA, digested to completion with Bam H1 and Nar 1, was run on preparative agarose gel to obtain a 1288 bp fragment coding for the C-terminal end of t-PA.

The 5' end of the t-PA gene was obtained by digestion of 10 μg of pWP 42 with four units of Hga 1 at 37° C. for eight hours. A 515 bp fragment was isolated by electrophoresis in 1% agarose gel. The cohesive ends of this DNA fragment were filled in with DNA polymerase 1 (Klenow fragment) and dNTPs and the product was ligated to Sma 1 cut pUC 13. After transforming E. coli JM 103 cells, approximately 75 ampicillin resistant, white colonies were obtained. Twenty-four of these colonies were grown to prepare a miniplasmid preparation. The miniplasmid preparation was digested with Nar 1 and 17 clones were found to have the required insert in either orientation. One clone (ptPHga 4) was grown in 1.0 liter of LB medium containing ampicillin to obtain a large quantity of plasmid DNA using the boiling method. The plasmid DNA, ptPHga 4, was digested with Bam H1 and Nar 1 and electrophoresed on 1.2% agarose gel to isolate a 434 bp DNA fragment coding for the N-terminal end of t-PA.

The 1288 bp DNA (300 ng) and 434 bp (100 ng) were ligated overnight to obtain a 1722 bp DNA fragment. This DNA, after ligation with Bam H1 cut pUC 13 was used to transform *E. coli* JM 103 cells. More than 1000 ampicillin resistant colonies were obtained. Plasmid DNA from twelve colonies was prepared by the boiling method. The plasmid DNA was identified by cutting with each of Bam H1, Nar 1 and Xho II. All of the resulting plasmids were found to contain the desired 1722 bp DNA fragment. One plasmid (ptPBM 1) was used for large scale plasmid DNA preparation. This plasmid, when cut with Bam H1, gave rise to the 1722 bp DNA coding for the complete t-PA molecule.

Screening and Identification of u-PA Clone

The library of $10^5$ recombinant bacterial clones from which the t-PA gene was derived, supra, was screened with a radiolabelled 18 mer probe by the method of Grunstein et al., Proc. Nat'l. Acad. Sci. USA, 72, 3961, (1975). The probe, synthesized by the standard phosphotriester method using a Gene Machine (Applied Biosystems), presents the oligomer sequence - 5'-GTA GAT GGC CGC AAA CCA - 3'- corresponding to the middle part of the urokinase gene (a.a.173-179). About 13 clones exhibited a moderate to strong hybridization signal. These clones were grown in 2 ml LB medium containing tetracycline and a miniplasmid preparation was prepared. The miniplasmid preparation was dissolved in 40 µl $H_2O$ containing 10 µg/ml RNAse. About 8 µl of the DNA thereby produced was digested with one unit of Pst 1 and the product separated by electrophoresis on 1% agarose gel. One clone (pUK 53) was found to contain the largest insert of 1.7 Kb in the form of three inserts of sizes 1.2, 0.4 and 0.1 Kb long. The complete 3' end nucleotide sequence of urokinase was present in the Pst 1 cut 1.2 Kb DNA fragment. The 5' end sequence of the gene was discovered, through nucleotide sequencing by the Maxam and Gilbert method, Methods Enzymol., 65, 1499 (1980) to be missing approximately 30 nucleotides corresponding to the first 10 amino acids of the signal peptide coding region of the urokinase protein. Therefore, a duplex DNA sequence corresponding to the missing nucleotides was synthesized and ligated to the existing gene.

pUKBM-1

The urokinase plasmid (pUK 53) DNA was cut with Nco 1 and Mst II and the products separated by electrophoresis on 1% agarose gel. A DNA fragment of 1198 bp was isolated by electroelution. The 5' protruding end of the DNA fragment corresponding to the Nco 1 cut was made blunt ended by filling in with dNTP's and *E. coli* DNA polymerase (Klenow fragment). The DNA was then ligated to Sma 1 cut pUC 13 and the modified plasmid was used to transform competent *E. coli* JM 103 cells. The Nco 1 site of the insert was regenerated when the DNA is ligated to the Sma 1 site of pUC 13. The cells were plated out on ampicillin and X-gal plates and a miniplasmid preparation was produced from white colonies. Digestion of the miniplasmid DNA preparation with Nco 1 and Sal 1 gave an approximate 1200 bp DNA fragment. A large scale plasmid DNA preparation from a positive clone (pUKNM-3') was made and digested with Nco 1 and Sal 1 to obtain a large amount of the approximate 1200 bp DNA fragment which was separated by preparative agarose gel electrophoresis.

To provide the approximate 30 nucleotides corresponding to the first 10 amino acids of the 5' signal peptide coding region of the urokinase protein, pUK 53 plasmid DNA was digested first with Pst 1 and a 400 bp DNA fragment was isolated. This DNA was then treated with ScrF1 to yield a 242 bp fragment of DNA. The protruding ends of the DNA were filled in with dNTP's and *E. coli* DNA polymerase 1 (Klenow fragment).

Two complementary oligonucleotide sequences, 38 and 42 bases in length, were synthesized on a Gene Machine to provide for missing amino acids (−9 to −20) while keeping the proper translational reading frame and providing a Sal 1 sequence on both ends of the DNA for subcloning in Sal 1 cut pUC 13. The two oligomers were mixed in equimolar amounts in ligase buffer (50 mM Tris.HCl, pH 7.6, 10 mM $MgCl_2$, 10 mM dithiothreitol) and heated to 80° C. for 5 minutes and allowed to cool to room temperature for about 1 hour. The thus formed duplex of the two complementary nucleotide sequences (about 1 µg) was ligated to about 300 ng of the 242 bp DNA fragment in ligase buffer at 4° C. for 16 hours using 400 units of T4 DNA ligase. The ligated mixture was separated by electrophoresis on 1.2% agarose gel and an approximate 320 bp DNA fragment was isolated by electroelution. This fragment (about 20 ng) was ligated to 100 ng of Sal 1 cut pUC 13 and the vector was used to transform competent *E. coli* JM 103 cells. The cells were plated out on ampicillin X-gal plates. Twelve white colonies were selected and grown to prepare a miniplasmid preparation. The miniplasmid preparation was cut with Sal 1. One clone, containing the expected 320 bp DNA insert, was grown for large scale preparation of plasmid DNA. The DNA is cut with Sal 1 and Nco 1 to yield a 260 bp DNA fragment upon preparative agarose gel electrophoresis.

The 260 bp DNA and 1200 bp DNA fragments containing a common Nco 1 restriction site at 333 bp position of the gene, were mixed in equimolar amounts for ligation. The ligated product was cut with Sal 1 and the reaction mixture separated by preparative 1% agarose gel electrophoresis. A 1460 bp DNA fragment was isolated by electroelution. This DNA was ligated to Sal 1 cut pUC 13 and the plasmid was used to transform competent *E. coli* JM 103 cells which were plated out on ampicillin and X-gal plates. Twelve white colonies were selected and grown to prepare a miniplasmid preparation by the boiling method. The miniplasmid preparation was cut with Sal 1 and one clone (pUKBM-1) was found to contain the desired 1460 bp DNA insert. pUKBM-1 was grown in large volume to provide plasmid DNA. The oligonucleotide sequence from the 5' end containing the synthetic linker was sequenced by the Maxam -Gilbert method to confirm its authenticity.

The DNA insert in pUKBM-1 plasmid was thereby established to contain the translational initiation codon ATG (met, −20 aa in the leader sequence) as well as the termination codon TGA. This complete gene codes for the 20 amino acids of the signal peptide (−1 to −20) and the 411 amino acids of the mature urokinase protein.

pUKKNd16

About 10 μg of pUK 53 plasmid DNA was digested to completion with Sca 1 which cuts at bp 204 in the urokinase sequence. After phenol extraction and ethanol precipitation, the DNA pellet was dissolved in 50 μl of buffer solution (10 mM CaCl$_2$, 12 mM MgCl$_2$, 0.2 M NaCl, 20 mM Tris.HCl (pH 8.0), 1 mM EDTA). To the reaction mixture was added 1 μl (2 units) of the exonuclease Bal 31 and the mixture was incubated at 30° C. for 15 seconds (Legerski, R. J., J. L. Hodnett, and H. B. Gray, Jr., Nucleic Acid Res. 5, 145, 1978). The reaction was stopped by the addition of 5 μl of 0.4M EGTA. This reaction time was found to be sufficient to remove about 80 bp from each end of the DNA fragment. After phenol extraction and ethanol precipitation, the DNA was ligated to an oligonucleotide linker (10 bp) under standard reaction conditions. The oligomer linker (EcoR1/Nde 1 linker) with the sequence, TGGAATTCCA, was designed to create an Nde 1 site (CATATG) when ligated to the DNA fragment end containing the sequence, TATG (corresponding to a.a. 51). In addition, the restriction site, EcoR1, was built into the linker to provide for subsequent cloning in a pUC 13 vector. After phenol extraction and ethanol precipitation, the DNA was digested with EcoR1 and separated by electrophoresis on 1% preparative agarose gel. A DNA band corresponding to 340 bp, was cut, eluted and ethanol precipitated. About 40 ng of this DNA was ligated with about 0.4 μg of EcoR1 cut pUC 13 vector DNA and used to transform competent E. coli JM 103 cells (Maniatis et al., loc. cit. p. 250). About 1,000 recombinant colonies were obtained from 10 plates. The bacterial colonies were replica-plated on nitrocellulose paper, and screened by in situ hybridization using a radioactive oligonucleotide probe (Grunstein et al. Proc. Nat'l. Acad. Sci. USA 72, 3961, 1975). The oligonucleotide probe used was 18 bp long (TTCCATATGAGG-GGAATG) and contains the first five nucleotides from the EcoR1/Nde 1 linker and the next 13 bases from the urokinase sequence corresponding to a.a 51 to 54. Twelve clones showed a moderate to strong signal on X-ray film. Miniplasmid DNA prepared from these 12 clones was digested with Nde 1 and separated by electrophoresis on 1% agarose gel. One clone, pUKKNd 16, was found to contain the newly generated Nde 1 site.

p5'HybF-5

About 10 μg ptPBM-1 plasmid DNA in a 50 μl reaction mixture was digested with Nar I to give rise to two DNA fragments—600 bp and 3,800 bp. The smaller Nat I fragment (600 bp) contained the intended DNA of 400 bp to be isolated. The reaction mixture was diluted to 100 μl volume with BAL 31 buffer to give a final concentration of 10 mM CaCl$_2$, 12 mM MgCl$_2$, 0.2M NACl, 20 mM Tris-Cl, pH 8.0, 1 mM EDTA. The reaction tube was incubated with 1 μl (2u) of BAL 31 for 10 seconds at 30° C. This incubation time was found to be sufficient for the removal of 50 bp from each end of the 600 bp DNA segment. This resulted in a decrease of the DNA size from 600 bp to 500 bp when run on a 1.2% agarose gel electrophoresis. The reaction was stopped by the addition of 5 μl 0.4 M EGTA. After phenol extraction and ethanol precipitation, the DNA was made blunt ended with E. coli polymerase 1 (Klenow) and dNTPs (dATP, dCTP, dGTP, dTTP) (Maniatis, et al., loc. cit. p. 109). The DNA was electrophoresed in 1.2% agarose gel and a 500 bp DNA segment was isolated. About 100 ng of this DNA was ligated overnight at 15° C. with 1 μg Of FspI/EcoRI olignoucleotide linker. As the name suggests, the linker, gca gaa ttc tgc, was designed to create an Fsp I site (TGC gca) when ligated to DNA ending with the sequence TGC (a.a. 92). In addition, an EcoRI sequence was built into the linker to provide a convenient site for subsequent cloning in an EcoRI/pUC 13 vector. After phenol extraction and ethanol precipitation, the DNA was digested thoroughly with EcoRI and a 400 bp DNA fragment was isolated from 1.2% agarose gel. Equimolar amounts of this DNA and EcoRI cut pUC 13 were ligated and the product was used to transform E. coli JM 103. Several thousand recombinant colonies were obtained. About 1,000 colonies in 10 plates were replicated on nitro-cellulose paper and screened by in situ hybridization using a radiolabeled oligonucleotide probe (Grunstein, et al., Proc. Nat'l. Acad. Sci. USA, 72, 3961, 1975). The probe used was 18 nucleotides in length and was designed to represent the nucleotide sequence generated at the DNA/linker junction. This almost ensured the elimination of all unwanted clones with different nucleotide sequences at the DNA/linker junctions. Almost 100 clones gave moderate to strong hybridization signals when exposed to x-ray film. Twelve clones were picked and grown to obtain a miniplasmid preparation. About 8 μl of the plasmid-containing solution was digested with 1 unit of Fsp I. Nine out of 12 clones had the newly generated Fsp I site. Depending upon the orientation of the insert in the vector, Fsp I digestion would show either 500 bp (clone No. 2, 3, 5, 9) or 150 bp (clone No. 1, 7, 8, 11, 12). Final confirmation came from nucleotide sequencing by the Maxam-Gilbert method (Methods Enzymol., 65, 1499, 1980) which showed the presence of an Fsp I recognition sequence TGC GCA in clone 2 which was designated ptPFsp-2 which contains the DNA encoding for amino acids corresponding to the complete signal sequence and a.a. 1–92 of the t-PA gene, with an Fsp I site (TGCGCA) at bp 465 (a.a. 92) position.

Figure 9:
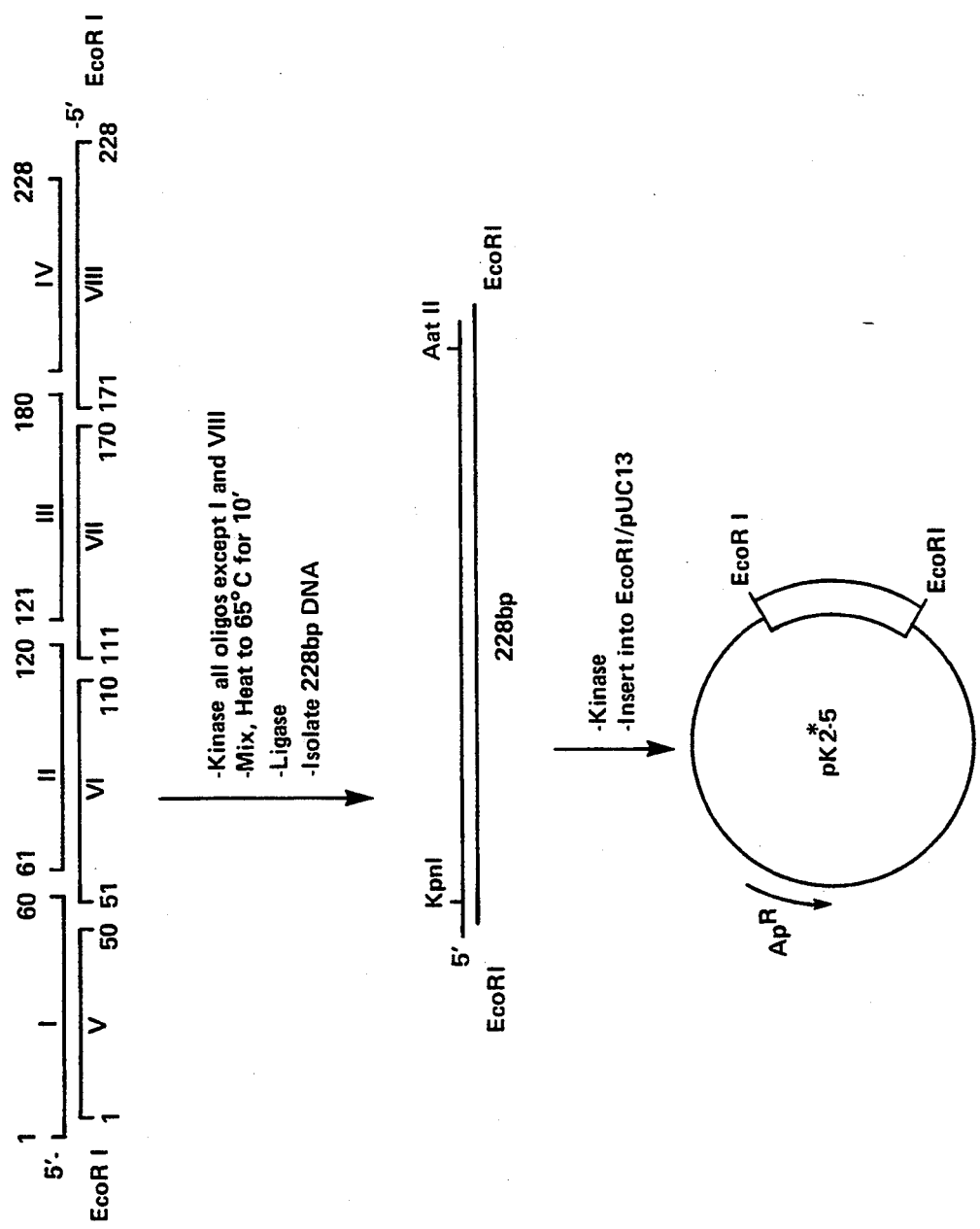

The DNA sequence corresponding to amino acids 191 through 258 found in the second kringle (K2) of tissue plasminogen activator (t-PA) as depicted in FIG. 8 was chemically synthesized by the preparation of eight overlapping oligonucleotides on the Gene Machine. The entire nucleotide sequence of oligomers I through VIII is depicted in FIG. 9. Oligomers V through VIII are complementary. A ten nucleotide overlap is provided in each fragment for duplex melding. Oligomers II through VII were phosphorylated with polynucleotide kinase and ATP. The 5'-end of oligos I and VIII were not phosphorylated to avoid self-ligation. All eight oligos were mixed in equal amounts (1 μg of each oligommer), heated to 65° C. for ten minutes for duplex formation among complementary strands and then ligated overnight at 15° C. with T4 DNA ligase. Phenol extraction and ethanol precipitation followed by electrophoresis on agarose gel located a 228 bp DNA product which, by construction was flanked on both 5' and 3' ends with EcoRI restriction sites and contains unique Kpn I and Aat II restriction site toward the 5' and 3' ends, respectively, the latter restriction sites defining the DNA fragment corresponding to a.a. 191 to 258 of t-PA. The 228 bp DNA product was electroeluted, phosphorylated with polynucleotide kinase and inserted into EcoRI cut pUC 13. A miniplasmid preparation from 12 clones was prepared and cut with EcoRI to identify the clones containing the desired 228 bp insert. One clone was chosen and designated pK2*-5. Nucleotide sequencing of the clone showed that the DNA containing the intending sequence was in correct reading frame. This DNA sequence contains alternate codon sequences for the desired amino acids to avoid recombination and looping out during transcription.

Figure 10A:
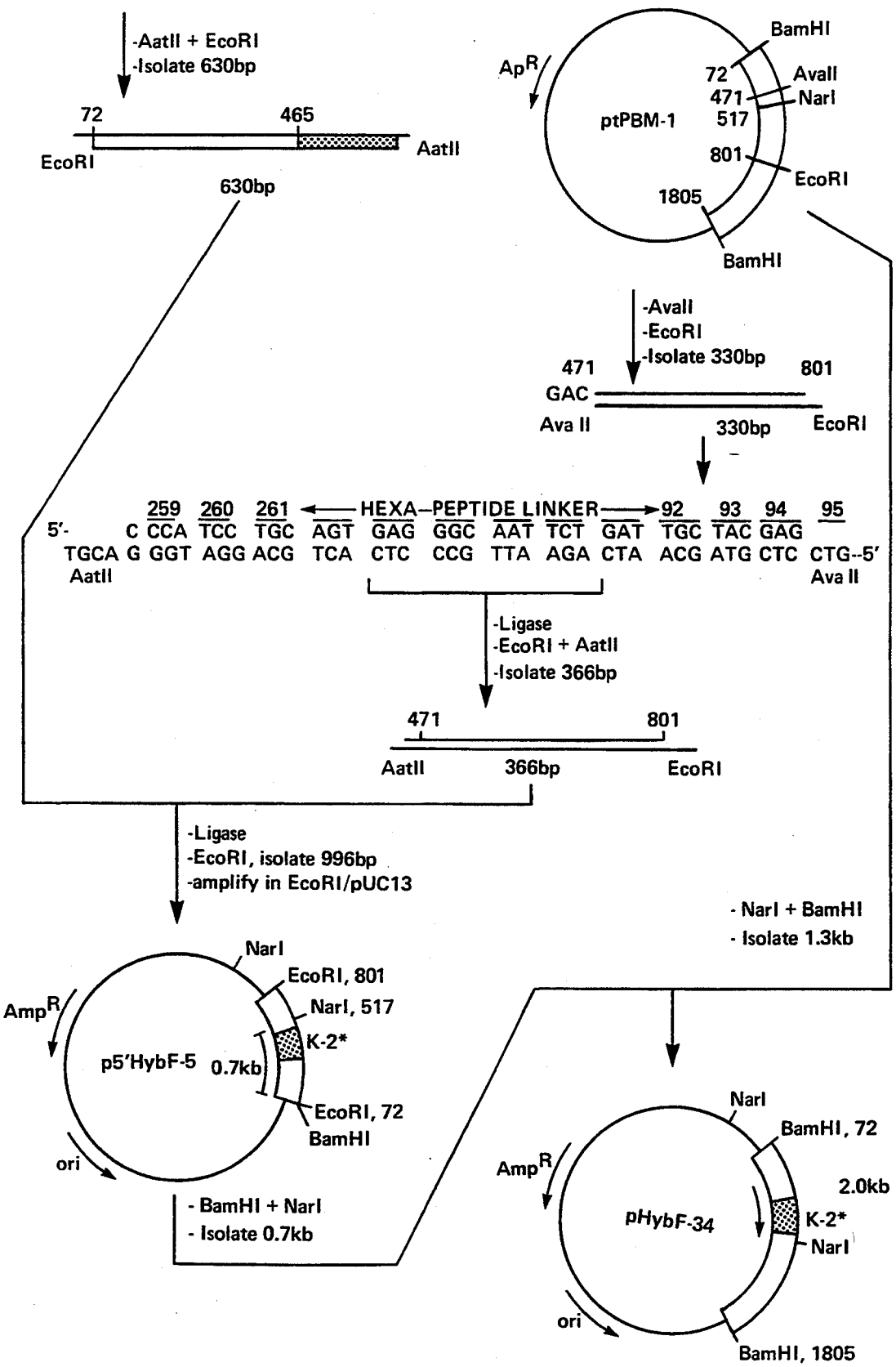
Figure 10:
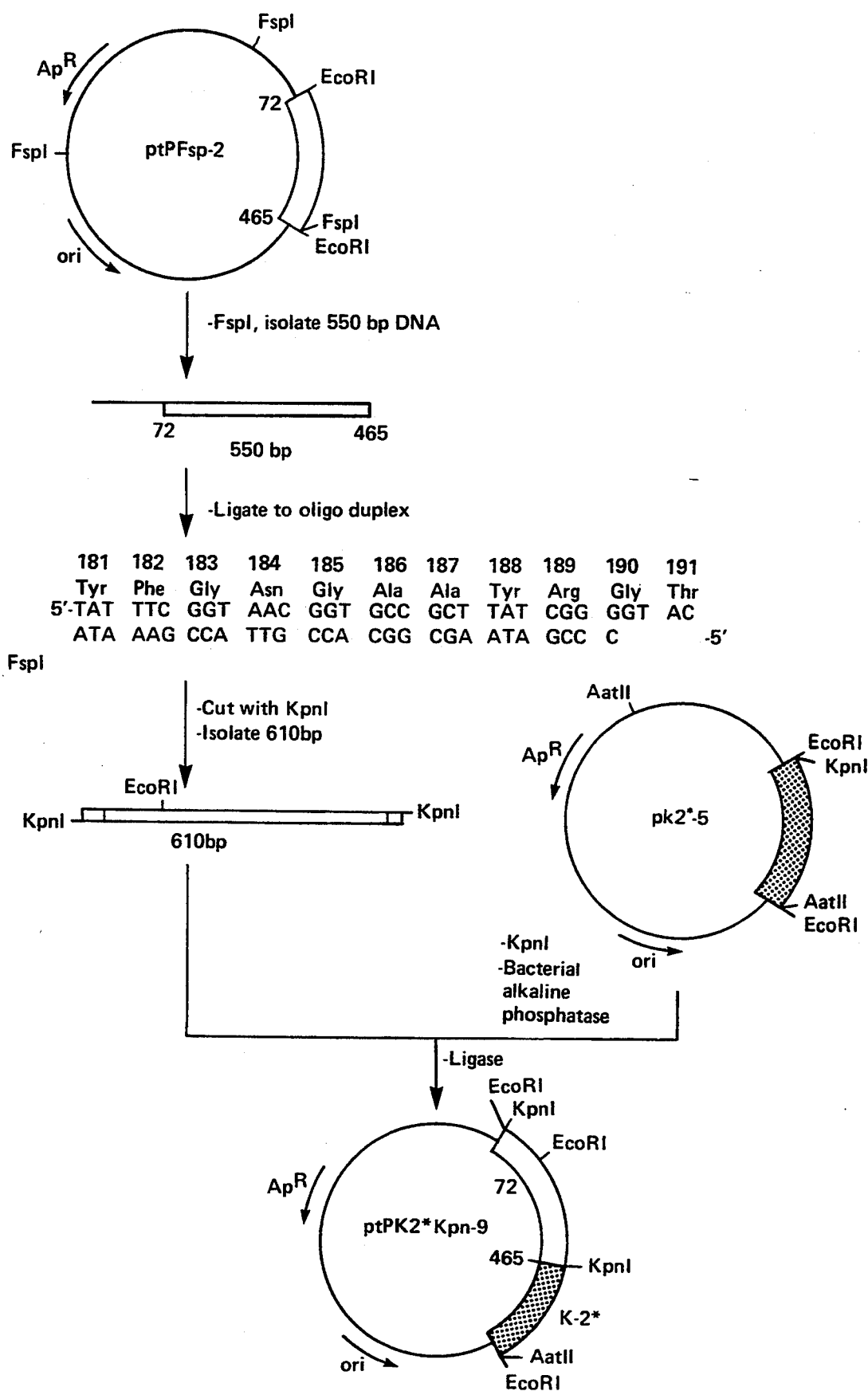
Figure 11:
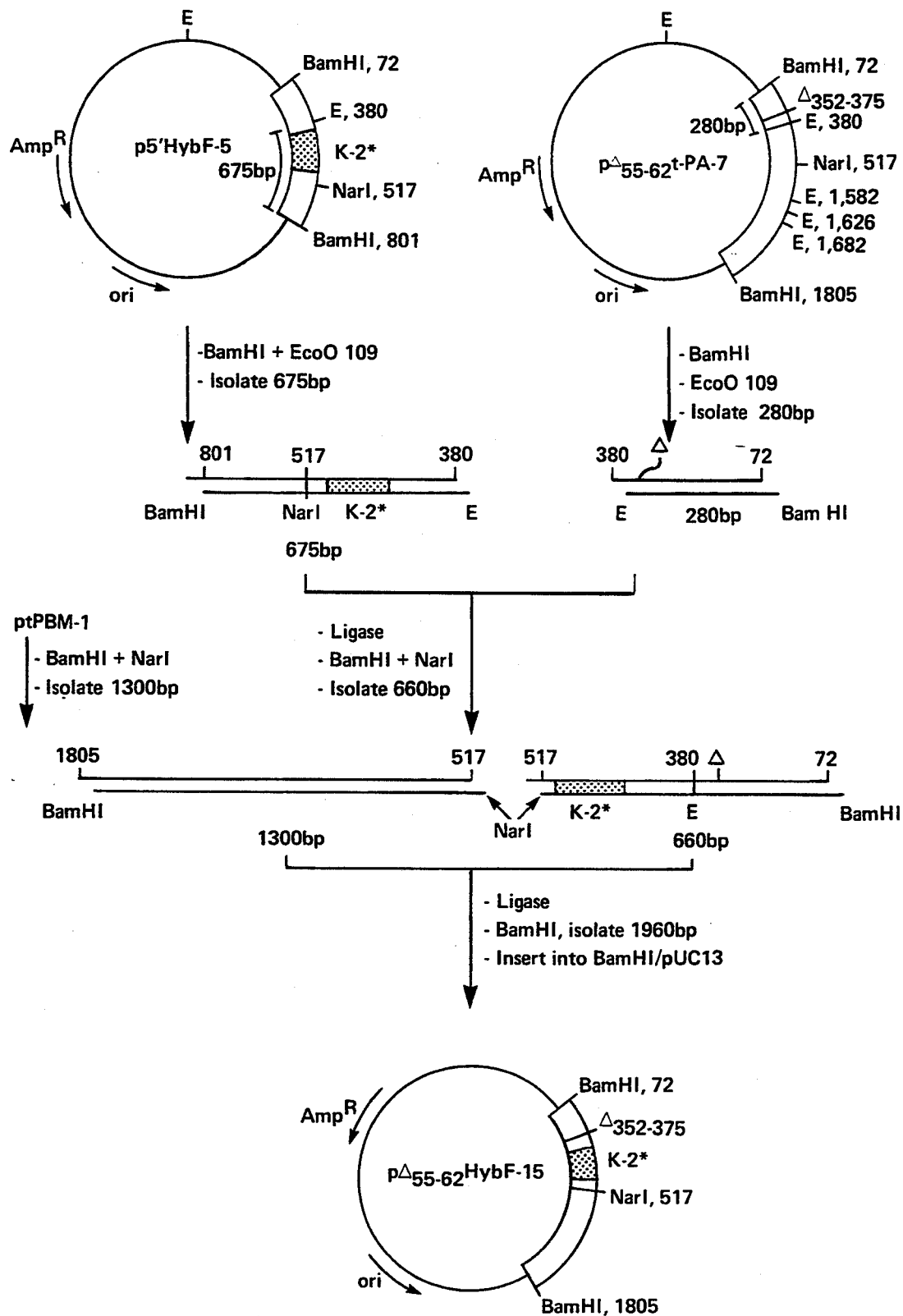
FIG. 11 presents a flow diagram of the method employed in the production of $42_{55-62}$-91-[Ala$^{186}$-K2]-92-t-PA.

About 10 μg of ptPFsp-2 was digested with Fsp-1 to provide a 550 bp DNA fragment encoding for the complete signal peptide (a.a. −35 to −1) and the first 92 amino acids of t-PA with the unique Fsp-1 restriction site at a.a. 92 position. About 1 μg of this DNA was ligated with T4 DNA ligase to 2 μg of duplex oligomer depicted in FIG. 10, produced on the Gene Machine to provide for production of the amino acid sequence -Tyr-Phe-Gly-Asn-Gly-Ala-Ala-Tyr-Arg-Gly-Thr- which corresponds to a.a. 181–191 of the second kringle of t-PA except for the presence of Ala in position 186, and to provide a Kpn-1 site (GGTACC) at the 3'-terminus. After phenol extraction and ethanol precipitation, the product was cut with Kpn-1 to isolate a 610 bp DNA fraction which was inserted into Kpn-1 cut pK2*-5 to obtain a recombinant clone in which the codon for the N-terminal part of the K2 kringle (a.a. 181–191) was joined to the codon providing amino acid 92 of t-PA. This recombinant clone was designated ptPK2*Kpn-9. It contains the nucleotide sequence encoding the complete signal sequence, a.a. 1–91 followed by a.a. 180–258 of K2 of t-PA. From this plasmid digested with Aat11 and EcoRI, was obtained the desired 630 bp DNA fragment.

A 330 bp DNA fragment (bp 471–801) containing information coding for a.a. 95 to 205 t-PA was isolated from EcoRI and Ava 11 cut ptPBM-1. This 330 bp DNA fragment was ligated to a duplex oligomer prepared on the Gene Machine encoding for amino acids 259 to 261 of K2*, the hexapeptide linker encoding for Ser-Glu-Gly-Asn-Ser-Asp and amino acids 92 to 95 of K1 of t-PA. The product was cut with EcoR1 and Aat11 and a 366 bp DNA fragment was isolated, which was ligated to the 630 bp DNA sequence produced in the preceding paragraph to obtain a 996 bp DNA fragment. This DNA sequence was inserted into EcoR1 cut pUC 13 for amplification and one recombinant clone was identified which contained the desired product. This clone was labeled p5'HybF-5.

EXAMPLE 1

Δ2-89 t-PA

About 10 μg of ptPBM-1 was digested with Bgl II and a 2.8 kb DNA fragment was isolated by preparative agarose gel electrophoresis. This fragment of DNA corresponds to the pUC vector and containing the complete signal peptide region (−35 to −1 amino acids) of t-PA.

To the Bgl II cut 2.8 kb DNA was ligated two chemically synthesized complementary oligonucleotide sequences of 20 and 19 bases:

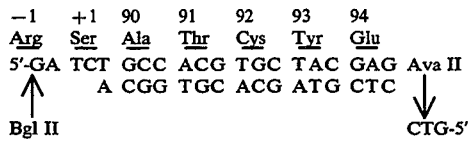

which provide for the indicated missing amino acids in and before t-PA kringle 1. This oligonucleotide linker sequence was designed to create Bgl II and Ava II restriction sites at 5'- and 3'- ends, respectively, when joined to a Bgl II and Ava II cut t-PA gene. The 20 base oligomer was phosphorylated with ATP and polynucleotide kinase. The two oligomers were then mixed in equimolar amounts in ligase buffer (50 mM Tris-HCl, pH 7.6, 10 mM MgCl$_2$, 10 mM DTT), heated to 80° C. for five minutes and allowed to cool to room temperature for about one hour. About 4 μg of the Bgl II cut 2.8 kb DNA was added to about 1 μg of the duplex linker and the mixture was incubated with T4 DNA ligase at 15° C. for about sixteen hours. After phenol extraction and ethanol precipitation, the product was digested thoroughly with EcoR1 and a 130 bp DNA fragment containing the leader sequence and linker was isolated.

About 10 μg of ptPBM-1 was digested with Ava II to isolate a 747 bp DNA fragment, (position 471 to 1218) by preparative 1% agarose gel electrophoresis. The 747 bp DNA fragment was then digested with EcoR1 to obtain a 330 bp DNA fragment (positions 471 to 801).

About 1 μg of each of the 130 bp DNA fragment and the 330 bp DNA fragment prepared in the preceding paragraphs were mixed and incubated in ligase buffer at 15° C. for about sixteen hours with T4 DNA ligase. Following extraction with phenol, ethanol was added to precipitate the product, which was then digested with EcoR1 to obtain a 460 bp DNA fragment. This DNA was ligated to EcoR1 cut pUC 13 and the product used to transform competent E. coli JM 103 cells, which were plated out on ampicillin and X-gal plates. Twelve recombinant (white) colonies were selected and grown in 1 ml of culture for miniplasmid preparations. The presence of the insert in the recombinant plasmid was checked by digestion with Ava II, Nar 1 or EcoR1 and Bgl II. Nine clones were found to contain the required insert oriented as shown in FIG. 1. Nucleotide sequencing of one of the clones (p5'-Δ$_{2-89}$-tP-4) by the Maxam-Gilbert method [Methods Enzymol., 65, 1499 (1980)] confirmed proper deletion of the undesired DNA sequence (positions 187–463).

To join the DNA sequence produced in the preceding paragraph with DNA coding for that portion of the t-PA gene beginning at position 517 while simultaneously creating a common Nar 1 restriction site at position 517, about 5 μg each of ptPBM-1 and p5'-Δ$_{2-89}$-tp-4 were digested with Nar 1 and Bam H1 to afford DNA fragments of 1300 bp and 200 bp, respectively. These two DNA fragments were ligated overnight at 15° C. and then digested with Bam H1 to isolate a 1500 bp DNA fragment containing the entire sequence coding for Δ$_{2-89}$-t-PA which was then inserted into the Bgl II site of p341-3. At the Bam H1 site of the resulting plasmid was inserted an 8 kb BPV genome DNA to obtain a complete BPV-dependent expression vector (p42 $_{2-89}$ tP-AMT-BPV-40). Conventional culture, recovery, isolation and purification techniques yield the plasminogen activator t-PA devoid of the fibronectin and epidermal growth factor region of amino acids 2 through 89. This plasminogen activator differs from that which would be produced from the DNA labeled LK1-2 by Van Zonneveld et al., loc. cit., at least by Ser in position 1, which appears in mature t-PA, and the presence of which is instrumental in the correct processing of the mature protein (Arg$^{-1}$-Ser$^{+1}$).

EXAMPLE 2

Δ$_{EGF}$t-pA

About 5 μg of ptPBM-1 was digested with Sty 1 to afford two DNA fragments of about 3.0 kb and 1.35 kb. The larger fragment, containing the 5' end of the t-PA gene (bp 72 to 350) was isolated by electroelution. This DNA fragment was digested with Bal 31 for five seconds to remove about eight bp from the 3' end to approximately bp 342 (. . . TGC) position which corresponds to amino acid number 51 of t-PA. The mixture resulting from digestion with Bal 31 was ligated to a synthetically prepared (Fsp 1 - EcoR1) linker, 5'-gcagaattctgc-3' which, when linked properly to the bp 342 . . . TGC sequence produces a new Fsp 1 restriction site ( . . . TGCgca . . . ). Complete digestion of the linker-tagged Bal 31 digestion product with EcoR1 yielded a mixture of DNA fragments of about 300 bp, which were isolated and inserted into Eco R1 cut pUC 13 and then used to transform E. coli JM 103 cells. These transformed cells were screened by in situ hybridization with a radiolabeled 21 mer probe synthesized to complement the nucleotide sequence generated at the junction of DNA and linker with twelve nucleotides corresponding to amino acids 48 to 51 of t-PA and nine nucleotides corresponding to the linker. Six clones exhibiting strong hybridization signals on X-ray film were cultured to obtain a miniplasmid preparation. The DNA was digested with Fsp 1 and run on 1.2% agarose gel electrophoresis. Three clones exhibited the presence of Fsp 1 restriction sites as evidenced by the presence of 150 bp and 450 bp DNA fragments, depending upon the orientation of the insert in the vector. Nucleotide sequencing by the Maxam-Gilbert method identified one clone, p1-51 tPFsp1, with the Fsp 1 site in the desired position corresponding to amino acid 51 of t-PA. Digestion of this plasmid with Fsp1 and EcoR1 gave rise to a 300 bp DNA fragment which corresponds to the first 51 amino acids and the complete leader sequence of t-PA.

About 10 μg of ptPBM-1 was digested with Ava II and a 747 bp DNA fragment was isolated by preparative 1% agarose gel electrophoresis. The cohesive ends were filled in with E. coli DNA Polymerase 1 (Klenow fragment) and dNTP, and the DNA was digested with EcoR1 to provide a DNA fragment of about 330 bp. About 0.5 μg of each of the 300 bp DNA fragment produced in the preceding paragraph and the 330 bp DNA fragment were blunt-end ligated with T4 DNA ligase and T4 RNA ligase at 4° C. overnight. The product mixture was extracted with phenol, precipitated with ethanol and cut with EcoR1 to provide a 630 bp DNA fragment. The 630 bp DNA fragment was inserted in EcoR1 cut pUC 13 and the plasmid was used to transform competent E. coli JM 103 cells. Eighteen recombinant clones were selected and grown for miniplasmid DNA preparations. The desired clone, p5'Δ$_{EGF}$-tP11, was identified by digestion of the plasmid DNA with EcoR1, Nar 1 or EcoR1 and Bgl II. Deletion of the EGF domain as well as restoration of the proper reading frame was confirmed by DNA sequencing of the selected clone by the Maxam-Gilbert method.

The plasmids, p5'Δ$_{EGF-tp}$-11 and ptPBM-1, were digested with Nar 1 and Bam H1 to isolate the 335 bp and 1,300 bp DNA fragments, respectively. About equimolar amounts of the two DNA fragments were ligated and then digested with Bam H1 to isolate a DNA fragment of about 1635 bp which was amplified in pUC 13 to obtain recombinant clone pΔ$_{EGF}$tP-pUC-22. This DNA contains the coding sequence for ΔEGF-tissue plasminogen activator. Insertion of this DNA sequence into the Bgl II site of p341-3, a BPV-dependent expression vector, followed by conventional culturing, recovery, isolation and purification yields t-PA devoid of the epidermal growth factor region corresponding to amino acids 52-91.

EXAMPLE 3

Δ$_{EGF}$-Urokinase

About 20 μg of pUKBM-1 was digested with Acc 1 and Nco 1 to obtain a 263 bp DNA fragment which was cut with Hinf 1. A 55 bp DNA fragment corresponding to positions 70 to 125 bp was isolated from the reaction product by electrophoresis.

About 10 μg of pUKKNd16 was digested with Nde 1 and a 550 bp DNA fragment was isolated.

Two complementary oligomers of 22 and 23 bases in length were synthesized and mixed in equal parts to provide a duplex oligomer flanked by Nde 1 and Hinf 1 restriction sites at the 3' and 5' ends, respectively, to provide the nucleotide bases for missing amino acids and a correct reading frame-in the gene. The duplex oligomer presented the nucleotide sequence:

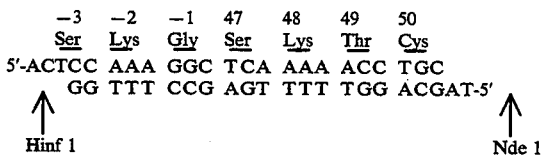

About 1 μg of this duplex oligomer was ligated to the 550 bp DNA fragment with T4 DNA ligase at 4° C. over a period of sixteen hours. After phenol extraction and ethanol precipitation, the product was digested with EcoR1 and a 360 bp DNA fragment was isolated.

Approximately equimolar amounts of the 55 bp DNA fragment and the 360 bp DNA fragment were ligated overnight and the product was digested with Acc 1 and EcoR1 to obtain a 415 bp DNA fragment which was inserted into an EcoR1 - Acc 1 cut pUC 13 plasmid. Amplification yielded a recombinant clone p5'Δ$_{1-46}$UK-1 which, when digested with Sal 1 and then Nco 1 provided a 125 bp DNA fragment which was ligated to a 1200 bp DNA fragment obtained by digesting pUKBM-1 with Sal 1 followed by Nco 1. The ligated DNA fragment was digested with Sal 1 to isolate a 1325 bp DNA sequence devoid of nucleotides 137-274, which encodes for the epidermal growth factor region of urokinase. This DNA fragment was amplified in pUC 13 to obtain the recombinant clone pΔ$_{EGF}$UK-1. Insertion of this DNA in the Bgl II site of a BPV-dependent expression vector, followed by conventional culturing, recovery, isolation and purification yields urokinase devoid of the epidermal growth factor region corresponding to amino acids 1 to 46.

EXAMPLE 4

Bi(amino acids 1-44), Δ$_{EGF}$t-PA

About 10 μg of p5'-Δ $_{EGF}$-tP-11, produced in Example 2, was digested with Bgl II to cut the DNA exactly at the junction of the signal peptide and the first amino acid of tPA (corresponding to the N-terminal site of the finger domain of t-PA), A 3.4 kb DNA fragment was isolated by electrophoresis on preparative 1.0% agarose gel. The product was dephosphorylated with bacterial alkaline phosphatase.

To the 3.4 kb DNA fragment was ligated a 132 bp DNA fragment (depicted in FIG. 4(b) and representing the entire fibronectin domain of t-PA) which was chemically synthesized by standard procedures following the sequence depicted in FIG. 4(a) wherein the eight oligomers (designed to prevent looping out by incorporation of different sets of triplet codon sequences to create significant heterologies between the two finger DNA sequences while coding for the same amino acid sequence) were individually phosphorylated with polynucleotide kinase and ATP, ligated overnight at 15° C. with T4 DNA ligase, recovered by phenol extraction and ethanol precipitation, and digested completely with Bgl II.

The product of ligation of equimolar amounts of the 3.4 kb and 132 bp DNA fragments was used to transform E. coli JM 103 cells which were cultured. Miniplasmid DNA preparations were made from twelve white colonies. Digestion of the miniplasmid DNA with Bgl II, followed by electrophoresis on 1.5% agarose gel and Maxam-Gilbert sequencing, identified one clone, p5′FΔ$_{EGF}$-tP-1 with the correct insert size and sequence. Digestion of this plasmid DNA with Bam H1 and Nar 1 afforded a fragment of DNA of about 450 bp.

About 10 μg of ptPBM-1 was cut with Nar 1 and Bam H1 and a 1.3 kb DNA fragment was isolated.

About equimolar amounts of the 1.3 kb material and the 450 bp DNA fragment were ligated and cut with Bam H1 to yield a 1.75 kb DNA fragment which was amplified in the Bam H1 cut pUC 13/E. coli JM 103 system. The product DNA encoded for bi (amino acids 1–44), Δ$_{EGF}$-t-PA complete with signal sequence.

The thusly prepared DNA was inserted in the Bgl II site of a BPV-dependent expression vector. Conventional culture, recovery, isolation and purification techniques yield the title product with two sequential (bi-amino acids 1–44) fibronectin domains and no EGF domain.

Exactly the same procedures are applicable to the production of Δ$_{EGF}$ polykringle plasminogen activators, employing as the starting material the polykringle plasminogen activators disclosed in U.S. Pat. No. 4,916,071, incorporated herein by reference. Employing HybA DNA from p438/E. coli MM294 (ATCC 67,175) as the starting material, deletion of the EGF domain by the method disclosed herein yields Δ$_{EGF}$-(UKaa$^{1-131}$-Ser-Glu-Gly-Asn-Ser-Asp)$^{1-91}$-t-PA. Similarly, employing HybB DNA from p504/E. coli MM294 (ATCC 67,174) affords Δ$_{EGF}$-91-(UKaa$^{50-131}$-Ser-Glu-Gly-Asn-Ser-Asp)-92-t-PA and employing HybC DNA from p113/E. coli MM294 (ATCC 67,176) affords Δ$_{EGF}$-261-(Ser-Glu-Gly-Asn-Ser-Asp-UKaa$^{50-131}$)-262-t-pA.

Similarly, plasminogen activators in which amino acids 55–62 have been removed from the EGF domain are prepared by recombinant means, as illustrated by the following examples.

EXAMPLE 5

Δ$_{55-62}$-91-(UKaa$^{50-131}$-Ser-Glu-Gly-Asn-Ser-Asp)-92 t-PA

In this construction, the DNA sequence coding for the 8 amino acid sequence, a.a. 55-62 of HybB-PA was deleted by site directed "loop out" mutagenesis. To accomplish this, the recombinant plasmid containing the coding sequence was obtained in single stranded (ss DNA) form from Bluescript plasmid pBSM13$^-$(Stratagene, San Diego, Calif.), an M13 modified vector which can be obtained either in single stranded or double stranded form depending upon whether helper phase R408 is present or not (Russel et al., Gene 45, 333, 1986; Yanisch-Perron et al., Gene 33, 109, 1985).

The HybB-PA gene flanked by Bam H1 sequences was inserted into the Bam H1 site of pBSM13$^-$which was then used to transform E. coli JM103 cells. White colonies containing the insert were picked, grown to isolate plasmid DNA and analyzed by digestion with Bam H1. One clone, pBS-42 contained the hybrid B gene in the same orientation as the T7 promotor, indicating that the ssDNA would be the (+) strand. The ssDNA form of this plasmid was obtained by growing this clone to an optical density of about 0.3 at 600 nanometers, followed by infecting it with helper phage R408 which, as a lyric phage kills the cells and releases the ssDNA vector in the medium. The cells were then spun down in an Eppendorf microfuge at full speed for 5 minutes and ssDNA was isolated from the supernatant liquid as described [Baldari C. and Cesareni, G. (1985) Gene 35, 27–32].

Figure 6:
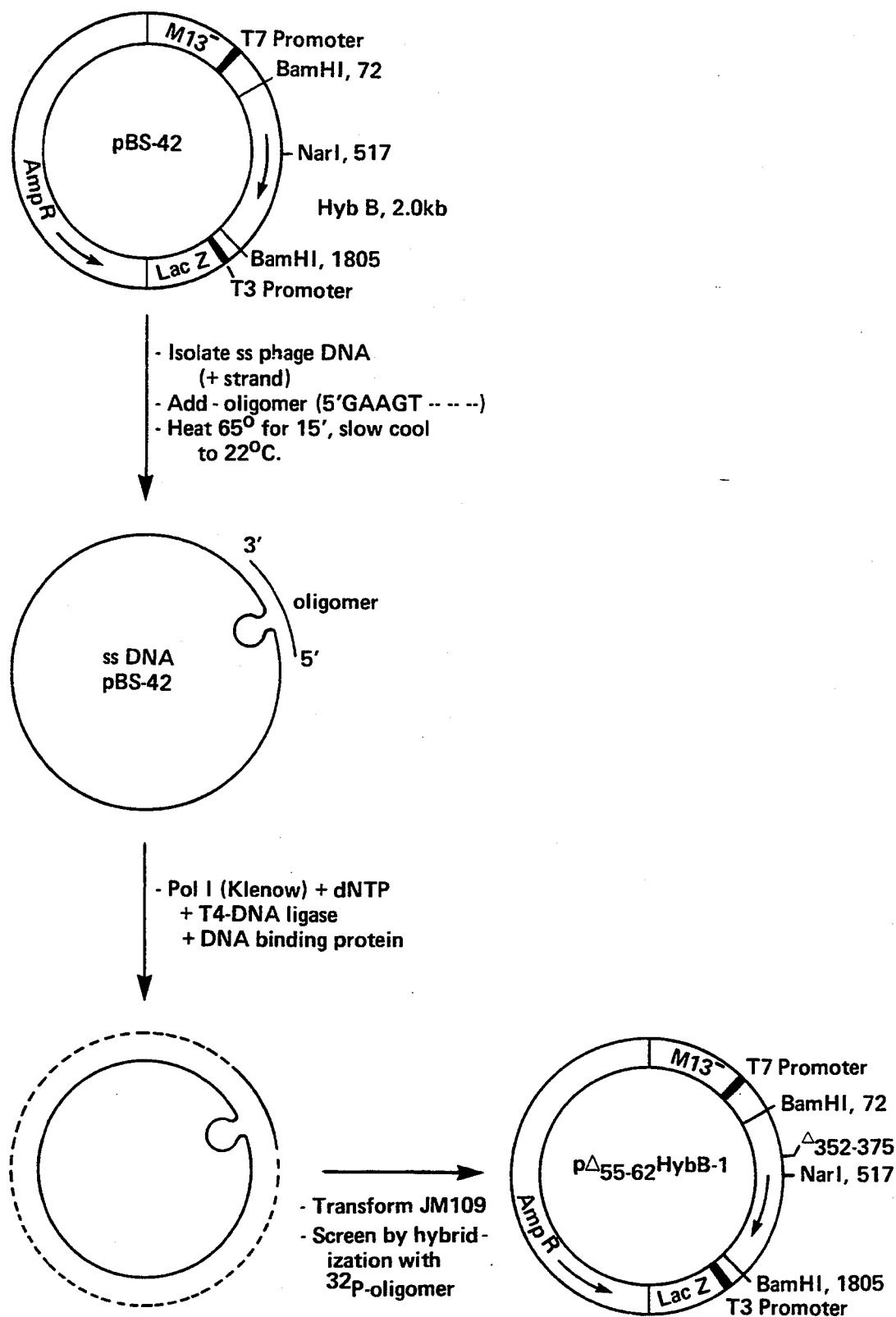
FIG. 6 presents a flow diagram of the method employed in the production of $\Delta_{55-62}$-91-(UKaa$^{50-131}$-Ser-Glu-Gly-Asn-Ser-Asp)-92-t-PA.

To loop out the DNA sequence corresponding to a.a. 55-62 (FIG. 6), the following 36 bp oligomer of the (−) or noncoding strand (lower one with sequence 3′-TTT . . . ) was synthesized.

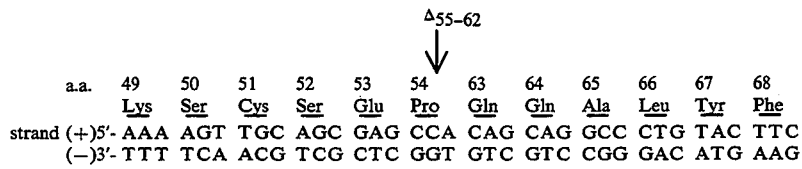

This oligomer sequence spans 18 bp on either side of the desired deletion to facilitate annealing with ssDNA pBS-42. About 100 ng of the oligomer was phosphorylated with ATP and polynucleotide kinase and annealed to approximately 1 μg of tile template ssDNA in ligation buffer (25 μl) by heating at 65° C. for 10 minutes and then slowly cooling to room temperature in 30 minutes. A synthesis reaction (elongation) was carried out at 15° C. for 6 hours with the following addition: 4 μl of 10× ligation buffer, 2 μl of 2.5 mM dNTP (N=A, C, G and T in equal amount), 4 μl of 10 mM ATP, 4 μl of gene 32 protein, 2 μl of Klenow Pol I, 1 μl of T4DNA ligase in a total volume of 40 μl. Ten μl of the synthesis reaction mixture was used to transform JM109 cells which were plated on an LB-agar plate containing ampicillin.

Screening for the desired clone was performed by in situ hybridization of colonies replicated on nitrocellulose filter paper with a $^{32}$P-radiolabeled oligo probe (same strand as used in the loop out reaction) under stringent conditions of hybridization. The filters were washed 3 times at 55° C. in low salt (0.2 XSSC) and exposed to x-ray film. The colonies exhibiting the highest hybridization signal were picked and grown to prepare miniplasmid DNA. Initial screening was performed by digestion of plasmid DNA with Sty 1, located at position a.a. 55 of HybB. Loss of the Sty 1 site was taken as the preliminary criterion for choosing a clone with the desired deletion sequence. Two clones pΔ55-62HybB-1 and -2 were subjected to DNA sequencing by the Maxam-Gilbert method and were found to have the desired deletion.

Following the procedure of Example 1, the 2 kb DNA obtained by digestion of pΔ55-62 HybB-1 with Bam H1 was inserted into the BPV dependent mammalian expression system. Conventional culture, recovery, isolation and purification techniques yield the title plasminogen activators.

EXAMPLE 6

Δ55-62 t-PA

Figure 7:
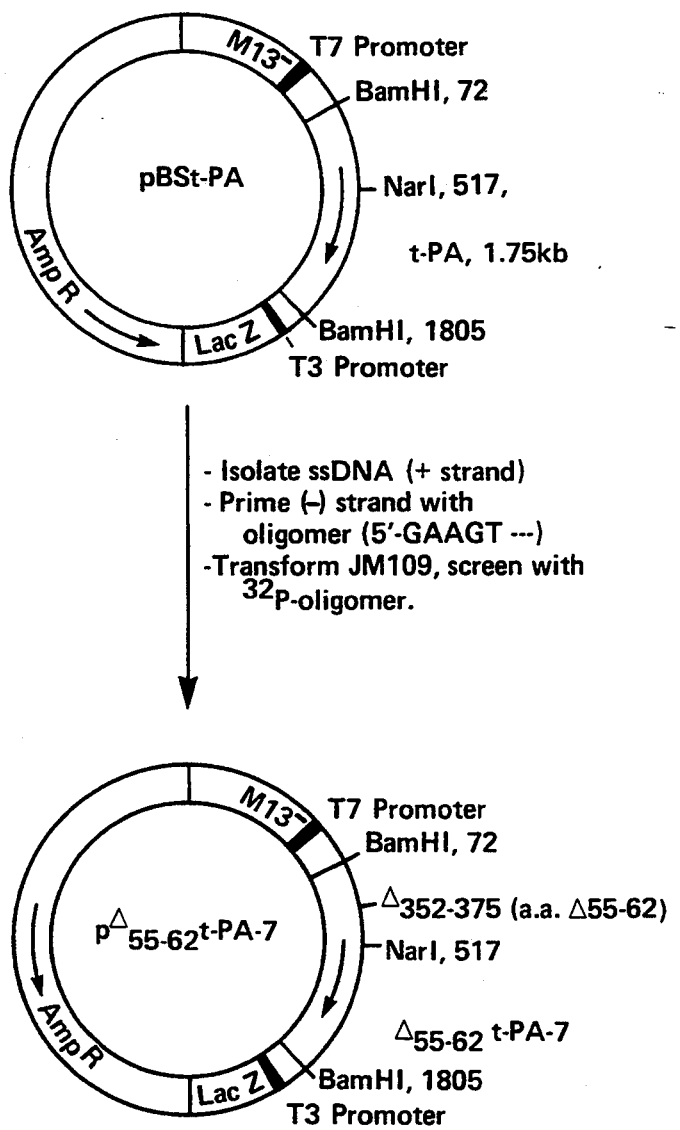
FIG. 7 presents a flow diagram of the method employed in the production of $\Delta_{55-62}$-t-PA.

Since the sequence to be deleted from t-PA is located in the EGF domain of both HybB-PA and t-PA, exactly the same reagents and approach was used to construct Δ55-62 t-PA. The t-PA gene, flanked by Bam H1 sequences at either ends, was first cloned into the pBSM13⁻ vector to obtain pBSt-PA which was used to produce ssDNA. To loop out the oligonucleotide sequence corresponding to a.a. 55-62, the same oligo as described in Example 5, was used to prime the second (—) strand of DNA and to screen the potential clones (FIG. 7). One clone, pΔ55-62 t-PA-7, was found by DNA sequencing to have the desired deletion.

Following the procedure of Example 1, the DNA obtained by digestion of pΔ55-62t-pA-7 with Bam H1 was inserted into the BPV dependent mammalian expression system. Conventional culture, recovery, isolation and purification techniques yield the title plasminogen activator.

EXAMPLE 7

Δ55-62-92-[Ala$^{186}$-K2]-92-t-PA p5'HybF-5 is a partial clone containing the bp 72-801 DNA segment of the HybF gene found in ATCC 67570. In this gene, a synthetic kringle (K-2*) sequence was inserted at bp 462/463 (a.a. 91/92) position of the t-PA gene. The deletion of 8 amino acids (a.a. 55-62) correspond to bp 352-375.

About 10 μg of p5'HybF-5 DNA was digested with Bam H1 and EcoO 109 to isolate a 675 bp DNA fragment which corresponds to Hybrid F bp 380-801 with K-2* inserted. About 20 μg of pΔ55-62t-PA-7 was digested first with Bam H1 to give rise to 1.7 kb and 2.6 kb DNA fragments. The 1.7 kb DNA fragment was further digested with EcoO 109 to isolate a 280 bp DNA fragment. The two DNA fragments, 675 bp and 280 bp, were ligated in equimolar amounts. Following phenol extraction and ethanol precipitation, the reaction mixture was digested with Nar 1 and Bam H1 to isolate a 660 bp DNA fragment. About 10 μg of ptPBM-1 was cut with Nar 1 and Bam H1 to isolate a 1,300 bp DNA fragment. The two DNA fragments, 660 bp and 1,300 bp, were ligated and cut with Bam H1 to isolate a 1960 bp sequence. This DNA was inserted into Bam H1 cut pUC13 which was then used to transform E. coli JM 109 cells. One recombinant clone, pΔ 55-62 HybF-15, was found to contain the complete gene corresponding to the title compound.

Following the procedure of Example 1, the genetic material obtained by digesting pΔ55-62 HybF-15 with Bam H1 is inserted into the BPV dependent mammalian expression system. Conventional culture, recovery, isolation and purification techniques yield the little plasminogen activator.

In comparison with t-PA, the Δ$_{EGF}$ and EGF modified plasminogen activators of this invention demonstrate marked reduction in affinity for liver membranes and as a result they are returned to circulation where they demonstrate a half-life in excess of thirty minutes, thereby assuring a constant supply of fibrinolytic material for recanalization of occluded arteries.

The Δ$_{EGF}$ and EGF modified plasminogen activators of this invention are used in treatment of vascular accidents in mammals in the same manner and through the same delivery vehicles as t-PA itself. Thus, the plasminogen activators of this invention may be formulated into pharmaceutical compositions by dissolving or suspending the polypeptides in suitable pharmaceutically acceptable vehicles known to the art as applied to t-PA. Administration to a mammal in need thereof by intravascular injection or infusion is conducted following techniques already established with t-PA itself. An intravenous primary dose of about 440 IU/kg/hr for about 6 to 12 hours is conventional practice when using t-PA.

The plasmids produced in Examples 1, 2 and 3 were deposited with the American Type Culture Collection, 12301 Parklawn Drive, Rockville, Md. 20852, on Jan. 21, 1987 and assigned the indicated accession numbers:

1. pΔ2-89tP-AMT-BPV-40 in E. coli HB-101 - ATCC 67299
2. pΔ$_{EGF}$tP-pUC-22 in E. coli JM-103 - ATCC 67300
3. pΔ$_{EGF}$UK-1 in E. coli JM-103 - ATCC 67301

The plasmids produced in examples 5, 6 and 7 were deposited in the same collection on Dec. 18, 1987 and assigned the following accession number:

5. pΔ55-62-91-(UK$_{aa}$$^{50-131}$-Ser-Glu-Gly-Asn-Ser-Asp)92-t--PA-BPV--14 in E. coli MM294 - ATCC 67588

6. pΔ55-62-t-PA-BPV 12 in E. coli MM294 - ATCC 67589

7. pΔ55-62-91-[Ala$^{186}$-K2]-92-t-PA-BPV-6 in E. coli MM294 - ATCC 67590

What is claimed is:

1. A plasminogen activator selected from the group consisting of

Δ$_{2-89}$-tissue plasminogen activator;

Δ$_{55-62}$-tissue plasminogen activator;

bifibronectin domain-Δ$_{52-94}$-tissue plasminogen activator,

Δ$_{1-46}$-urokinase;

Δ$_{1-46}$-(UKaa$^{1-131}$-Ser-Glu-Gly-Asn-Ser-Asp)$^{1-91}$-t-PA;

Δ$_{52-94}$-91-(UKaa$^{50-131}$-Ser-Glu-Gly-Asn-Ser-Asp)-92-t-PA;

Δ$_{55-62}$-91-(UKaa$^{50-131}$-Ser-Glu-Gly-Asn-Ser-Asp)-92-t-PA;

Δ$_{52-94}$-261-(Ser-Glu-Gly-Asn-Ser-Asp-UKaa$^{50-131}$)-262-t-pA;

Δ$_{55-62}$-261-(Ser-Glu-Gly-Asn-Ser-Asp-UKaa$^{50-131}$)-262-t-PA; and

Δ$_{55-62}$-91-[Ala$^{186}$-K2]-92-t-PA.

2. A plasminogen activator of claim 1 which is Δ$_{2-89}$-tissue plasminogen activator.

3. A plasminogen activator of claim 1 which is Δ$_{55-62}$-tissue plasminogen activator.

4. A plasminogen activator of claim 1 which is bifibronectin domain- Δ$_{52-94}$-tissue plasminogen activator.

5. A plasminogen activator of claim 1 which is $\Delta_{1-46}$urokinase.

6. A plasminogen activator of claim 1 which is $\Delta_{1-46}$-(UKaa$^{1-131}$-Ser-Glu-Gly-Asn-Ser-Asp)$^{1-9}$-t-pA.

7. A plasminogen activator of claim 1 which is $\Delta_{52-94}$-91-(UKaa$^{50-131}$-Ser-Glu-Gly-Asn-Ser-Asp)-92-t-PA.

8. A plasminogen activator of claim 1 which is $\Delta_{55-62}$-91-(UKaa$^{50-113}$-Ser-Glu-Gly-Asn-Ser-Asp)-92-t-pA.

9. A plasminogen activator of claim 1 which is $\Delta_{52-94-261}$-(Ser-Glu-Gly-Asn-Ser-Asp-UKaa$^{50-131}$)-262-t-PA.

10. A plasminogen activator of claim 1 which is $\Delta_{55-62-261}$-(Ser-Glu-Gly-Asn-Ser-Asp-UKaa$^{50-131}$)-262-t-PA.

11. A plasminogen activator of claim 1 which is $\Delta_{55-62-91}$-[Ala$^{186}$-K2]-92-t-PA.

* * * * *